US012796931B2

(12) United States Patent
Lewis et al.

(10) Patent No.: US 12,796,931 B2
(45) Date of Patent: Nov. 17, 2026

(54) GENERATING IMAGING-BASED NEUROLOGICAL STATE BIOMARKERS AND ESTIMATING CEREBROSPINAL FLUID (CSF) DYNAMICS BASED ON COUPLED NEURAL AND CSF OSCILLATIONS DURING SLEEP

(71) Applicant: THE GENERAL HOSPITAL CORPORATION, Boston, MA (US)

(72) Inventors: Laura Lewis, Boston, MA (US); Bruce Rosen, Charlestown, MA (US); Jonathan R. Polimeni, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 771 days.

(21) Appl. No.: 17/602,246

(22) PCT Filed: Apr. 13, 2020

(86) PCT No.: PCT/US2020/027963
§ 371 (c)(1),
(2) Date: Oct. 7, 2021

(87) PCT Pub. No.: WO2020/210813
PCT Pub. Date: Oct. 15, 2020

(65) Prior Publication Data

US 2022/0183561 A1 Jun. 16, 2022

Related U.S. Application Data

(60) Provisional application No. 62/832,771, filed on Apr. 11, 2019.

(51) Int. Cl.
*A61B 5/00* (2006.01)
*A61B 5/02* (2006.01)
(Continued)

(52) U.S. Cl.
CPC ........ *A61B 5/0042* (2013.01); *A61B 5/02007* (2013.01); *A61B 5/0205* (2013.01);
(Continued)

(58) Field of Classification Search
CPC . A61B 5/0042; A61B 5/02007; A61B 5/0205; A61B 5/055; A61B 5/14542;
(Continued)

(56) References Cited

U.S. PATENT DOCUMENTS 5,551,431 A * 9/1996 Wells, III ........... G01R 33/5659 324/309
8,571,634 B2 * 10/2013 Hubbard ................ A61B 5/026 324/309
(Continued)

FOREIGN PATENT DOCUMENTS

WO 2008137161 A2 11/2008
WO 2018112269 A1 6/2018

OTHER PUBLICATIONS

Dagli et al., "Localization of Cardiac-Induced Signal Change in fMRI", 1998 (Year: 1998).*
(Continued)

*Primary Examiner* — Adil Partap S Virk
(74) *Attorney, Agent, or Firm* — QUARLES & BRADY LLP

(57) ABSTRACT

An imaging-based biomarker that indicates a neurological state of a subject is generated from magnetic resonance imaging data acquired from the subject while the subject was sleeping, or during both a sleep state and wake state. These magnetic resonance imaging data are acquired in such a way so that they simultaneously enable measurement of cerebrospinal fluid ("CSF") flow and blood-oxygenation-level dependent ("BOLD") signals. The imaging-based biomarker can be generated based on a correlation between
(Continued)

CSF signals and BOLD signals extracted from these magnetic resonance imaging data. Using electroencephalography ("EEG") data, CSF flow dynamics can also be estimated based on a physiological model in which coherent neural activity is modeled as entraining oscillations in blood volume and CSF.

13 Claims, 16 Drawing Sheets
(9 of 16 Drawing Sheet(s) Filed in Color)

(51) Int. Cl.

| | |
|---|---|
| ***A61B 5/0205*** | (2006.01) |
| ***A61B 5/055*** | (2006.01) |
| ***A61B 5/145*** | (2006.01) |
| ***A61B 5/374*** | (2021.01) |
| ***G01R 33/48*** | (2006.01) |
| ***G06T 7/00*** | (2017.01) |

(52) U.S. Cl.
CPC .......... *A61B 5/055* (2013.01); *A61B 5/14542* (2013.01); *A61B 5/374* (2021.01); *A61B 5/4088* (2013.01); *A61B 5/4809* (2013.01); *A61B 5/704* (2013.01); *G01R 33/4806* (2013.01); *G06T 7/0012* (2013.01); *G06T 2207/10088* (2013.01); *G06T 2207/30016* (2013.01)

(58) Field of Classification Search
CPC ..... A61B 5/374; A61B 5/4088; A61B 5/4809; A61B 5/032; G01R 33/4806; G06T 7/0012; G06T 2207/10088; G06T 2207/30016
See application file for complete search history.

(56) References Cited

U.S. PATENT DOCUMENTS

| | | | | |
|---|---|---|---|---|
| 10,588,561 | B1 * | 3/2020 | Vale | A61B 5/0042 |
| 2005/0256397 | A1 * | 11/2005 | De Leon | A61B 5/4088 600/407 |
| 2006/0135868 | A1 | 6/2006 | Salomon et al. | |
| 2007/0055136 | A1 | 3/2007 | Yamamoto et al. | |
| 2010/0087730 | A1 * | 4/2010 | Yamada | A61B 5/055 600/419 |
| 2013/0204139 | A1 | 8/2013 | Kashif et al. | |
| 2013/0231552 | A1 * | 9/2013 | Grady | A61B 5/0042 600/410 |
| 2013/0266200 | A1 * | 10/2013 | Miyazaki | A61B 5/055 382/131 |
| 2014/0121498 | A1 | 5/2014 | Hubbard | |
| 2016/0367166 | A1 * | 12/2016 | Piron | A61B 5/031 |
| 2017/0128025 | A1 * | 5/2017 | Chen | A61B 5/0263 |
| 2017/0251950 | A1 | 9/2017 | Piron et al. | |
| 2017/0311870 | A1 | 11/2017 | Bardakjian et al. | |
| 2017/0343634 | A1 * | 11/2017 | Lencz | G01R 33/4806 |
| 2019/0083302 | A1 | 3/2019 | Khanna | |
| 2019/0246915 | A1 * | 8/2019 | Thiebaut Lonjaret | G01R 33/4806 |
| 2019/0274575 | A1 * | 9/2019 | Kim | A61B 5/055 |
| 2019/0357770 | A1 * | 11/2019 | Jordan | A61B 5/6803 |
| 2021/0282697 | A1 * | 9/2021 | Lee | A61B 5/055 |
| 2021/0343008 | A1 * | 11/2021 | Okuda | A61B 5/055 |
| 2022/0268867 | A1 * | 8/2022 | Reich | A61B 5/0042 |

OTHER PUBLICATIONS

Luh et al., "Comparison of Simultaneously Measured Perfusion and BOLD Signal Increases During Brain Activation With T1-Based Tissue Identification", 2000 (Year: 2000).*
Wise et al., "The Role of fMRI in Drug Discovery", 2006 (Year: 2006).*
He et al., "Quantitative BOLD: Mapping of Human Cerebral Deoxygenated Blood Volume and Oxygen Extraction Fraction: Default State", 2007 (Year: 2007).*
Jin et al., "Change of the cerebrospinal fluid vol. during brain activation investigated by T1p-weighted fMRI", 2010 (Year: 2010).*
Pflugfelder et al., "On the numerically predicted spatial BOLD fMRI specificity for spin echo sequences", 2011 (Year: 2011).*
Kasper et al., "Matched-filter acquisition for BOLD fMRI", 2014 (Year: 2014).*
Vitali et al., "Integration of multimodal neuroimaging methods: a rationale for clinical applications of simultaneous EEG-fMRI", 2015 (Year: 2015).*
Lanka et al., "Resting state fMRI data from subjects scanned with the EPI-PACE(Echoplanar Imaging—Prospective Acquisition Correction)sequence", 2018 (Year: 2018).*
Abreu et al., "EEG-Informed fMRI: A Review of Data Analysis Methods", 2018 (Year: 2018).*
Dipasquale et al., "Comparing resting state fMRI de-noising approaches using multi- and single-echo acquisitions", 2017 (Year: 2017).*
Jahanian et al., "Measuring vascular reactivity with resting-state blood oxygenation level-dependent (BOLD) signal fluctuations: A potential alternative", 2017 (Year: 2017).*
Zhang et al., "Comparison of Resting-State Brain Activation Detected by BOLD, Blood Volume and Blood Flow", 2018 (Year: 2018).*
Kiviniemi et al., "Comparison of methods for detecting nondeterministic BOLD fluctuation in fMRI", 2004 (Year: 2004).*
Fultz et al., "Coupled electrophysiological, hemodynamic, and cerebrospinal fluid oscillations in human sleep", 2019 (Year: 2019).*
Jin et al. "Change of the cerebrospinal fluid vol. during brain activation investigated by T1p-weighted fMRI," Neuroimage, Mar. 22, 2010 (Mar. 22, 2010), vol. 51, No. 4, pp. 1378-1383.
Bright et al. "Early anti-correlated BOLD signal changes of physiologic origin," NeuroImage, Nov. 5, 2013 (Nov. 5, 2013), vol. 15, No. 87, pp. 287-296.
Cabral et al. "Role of Local Network Oscillations in Resting-State Functional Connectivity," Neuroimage, Apr. 12, 2011 (Apr. 12, 2011), vol. 57, No. 1, pp. 130-139.
Battal et al. "Cerebrospinal fluid flow imaging by using phase-contrast MR technique," British Journal of Radiology, Aug. 31, 2011 (Aug. 31, 2011), vol. 84, No. 1004, pp. 758-765.
Harrison et al. "Non-invasive imaging of CSF-mediated brain clearance pathways via assessment of perivascularfluid mov\!ment with diffusion tensor MRI," elife, Jul. 31, 2018 (Jul. 31, 2018), vol. 7, e34028, pp. 1-14.
PCT/US2020/027963—International Search Report and Written Opinion—Jul. 6, 2020.
Abreu et al. "EEG Synchronization Measures Predict Epilepsy-Related BOLD-fMRI Fluctuations Better Than Commonly Used Univariate Metrics," Clinical Neurophysiology, Jan. 11, 2018 (Jan. 11, 2018), vol. 129, No. 3, pp. 618-635.
Hadjiabadi et al. "Brain tumors disrupt the resting-state connectome," NeuroImage: Clinical, Feb. 28, 2018 (Feb. 28, 2018), vol. 18, pp. 279-289.
Lenfeldt et al. "Cerebrospinal Fluid Pulse Pressure Method: A Possible Substitute for the Examination of B Waves," Journal of Neurosurgery, Dec. 31, 2004 (Dec. 31, 2004), vol. 101, No. 6, pp. 944-950.

* cited by examiner

GENERATING IMAGING-BASED NEUROLOGICAL STATE BIOMARKERS AND ESTIMATING CEREBROSPINAL FLUID (CSF) DYNAMICS BASED ON COUPLED NEURAL AND CSF OSCILLATIONS DURING SLEEP

CROSS-REFERENCE TO RELATED APPLICATIONS

This application is a U.S. National Stage of International Application No. PCT/US2020/027963 filed Apr. 13, 2020 which claims the benefit of U.S. Provisional Patent Application Ser. No. 62/832,771 filed on Apr. 11, 2019, and entitled "Coupled Neural and CSF Oscillations During Sleep," which is herein incorporated by reference in its entirety.

STATEMENT REGARDING FEDERALLY SPONSORED RESEARCH

This invention was made with government support under MH111748 awarded by the National Institutes of Health. The government has certain rights in the invention.

BACKGROUND

Sleep is important for both cognition and physiological maintenance of healthy brain function. Slow waves in neural activity contribute to memory consolidation, while the glymphatic system clears metabolic waste products from the brain. How these two processes are related is not well-known.

During human non-rapid eye movement ("NREM") sleep, the electroencephalogram ("EEG") exhibits low-frequency oscillatory dynamics, slow (0.1-1 Hz) oscillations and delta waves (0.5-4 Hz), which support memory consolidation and neuronal computation. In addition, functional magnetic resonance imaging ("fMRI") studies measuring blood-oxygenation-level-dependent ("BOLD") signals have demonstrated widespread hemodynamic signal alterations during NREM sleep. Important non-neuronal processes also occur during sleep. Recent studies have shown that sleep is associated with increased interstitial fluid volume and clearance of metabolic waste products into the CSF, and that clearance is stronger in sleep with more low-frequency EEG oscillations. Why these diverse physiological processes co-occur within this state of low arousal is not known; however, data described in the present disclosure show that CSF dynamics relate directly to the major changes in neural activity and hemodynamics that occur during sleep, and hence can be used as a marker of these important physiological states.

SUMMARY OF THE DISCLOSURE

The present disclosure addresses the aforementioned drawbacks by providing a method for generating an imaging-based biomarker indicative of neurological state of a subject, which may include a neurovascular state of the subject or an assessment of a drug delivery dynamic in the subject. Magnetic resonance imaging data are acquired from a subject using a magnetic resonance imaging ("MRI") system while the subject is in at least one of a sleep state or a wake state. Blood-oxygenation-level dependent ("BOLD") signal data are generated by extracting BOLD signals from the magnetic resonance imaging data using a computer system. Cerebrospinal fluid ("CSF") signal data are also generated by extracting CSF signals from the magnetic resonance imaging data using the computer system. An imaging-based biomarker is generated based on computing a correlation between the BOLD signal data and the CSF signal data, wherein the imaging-based biomarker indicates a neurological state of the subject.

It is another aspect of the present disclosure to provide a method for estimating CSF flow dynamics from electroencephalography ("EEG") data acquired from a subject. The EEG data are acquired from a subject's brain while the subject is in a sleep state. Slow-wave EEG signal data are generated from the EEG data by extracting slow-wave EEG signals from the EEG data using a computer system. CSF flow dynamics data are then generated using the computer system by inputting the slow-wave EEG signal data to a physiological model, in which coherent neural activity is modeled as entraining oscillations in blood volume and CSF, generating output as estimated CSF flow dynamics data. The CSF flow dynamics data can then be output to a user.

It is still another aspect of the present disclosure to provide a method for generating an imaging-based biomarker indicative of neurological state of a subject. The method includes acquiring magnetic resonance imaging data from a subject using an MRI system while the subject is in at least one of a sleep state or a wake state. CSF signal data are generated by extracting CSF signals from the magnetic resonance imaging data using a computer system. An imaging-based biomarker is then generated using the computer system based on the CSF signal data, wherein the imaging-based biomarker indicates a neurological state of the subject.

It is yet another aspect of the present disclosure to provide a method for estimating physiological signal data from magnetic resonance imaging data acquired from a subject using an MRI system. Magnetic resonance imaging data are acquired from the subject using the MRI system while the subject is in at least one of a sleep state or a wake state. Physiological signal data representative of a first physiological source are generated by extracting physiological signals from the magnetic resonance imaging data using the computer system. Additional physiological signal data representative of a second physiological source are then generated from the physiological signal data. The physiological signal data and the additional physiological signal data can be displayed to a user.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A: Example scan positioning in one subject: yellow box overlay shows position of the functional acquisition volume relative to the anatomical image. The bottom of the functional acquisition intersects with the fourth ventricle (red arrow), allowing inflow to be measured as bright signal in these lower slices. Only a subset of the 40 acquired slices are shown for display. FIG. 1B: Example image from the bottom slice of the functional volume: the inflow through the ventricle is detected as a bright signal (red arrow). FIG. 1C: EEG spectrogram from this subject shows stable periods of NREM sleep and wake (signaled by the ~10 Hz occipital alpha rhythm during wake). FIG. 1D: Behavioral task performance in this subject confirms sleep/wake segmentation. FIG. 1E: Time-series of a single voxel in the ventricle (temporally smoothed with 10-TR kernel) shows large slow pulsatile dynamics in sleep, that subside during the wake period, which exhibits a smaller and faster rhythm synchronized to respiration. FIG. 1F: Occipital EEG across wake vs. sleep segments confirms high delta power in sleep, as opposed to high alpha power in wake (n=13 subjects sleep; 11 subjects wake). Shaded region is 95% CIs; red lines mark non-overlapping CIs. FIG. 1G: Spectrum of ventricle signal across all subjects scanned at 3T shows increased 0.05 Hz power during sleep (n=13 subjects sleep; 11 subjects wake). Shaded region is 95% CIs; red lines and star mark non-overlapping CIs. FIG. 1H: Low-frequency power in the ventricle increased during sleep (n=13 sleep; 11 wake). FIG. 1I: This sleep-selective power increase was specific to the ventricle and not observed in a neighboring cerebellar ROI positioned on the same edge slices (n=13 sleep; 11 wake).

FIG. 2A: Schematic of acquisition: new CSF flowing into the imaging volume will generate bright signals. FIG. 2B: Inflow signals will be largest in the bottom slice, and decrease in amplitude inwards. If flow exceeds the critical velocity, then CSF in the bottom slice is completely replaced and signal amplitudes are large in inner slices as well. FIG. 2C: Mean amplitude across slices decays in ascending slices. Error bars are standard error across all segments with the ROI present in 4 contiguous slices (n=129 segments, 11 subjects). FIG. 2D: Example time-series from the bottom slices of the imaging volume in the 4th ventricle demonstrates largest and earliest signal in the lower (e.g. 2nd) slices and smaller signals in higher (e.g. 4th) slices, consistent with a pattern of CSF inflow. Orange arrows point out inflow events of varying amplitude: lower flow velocities lead to signals that decay in upper slices, whereas higher flow velocities can cause maximum signal to be reached in the inner slices as well.

FIG. 3A: Example fMRI time-series of the mean BOLD signal across all cortical gray matter, and the mean ventricle signal, from one subject scanned at 3T. During wake, gray matter BOLD and ventricle CSF signals are low-amplitude. FIG. 3B: During sleep, a large-amplitude BOLD oscillation appears, and its time-course is coupled to the ventricle CSF signal (~0.05 Hz). FIG. 3C: The mean cortical gray matter BOLD signal power across subjects increases during sleep (n=11 subjects for pairwise tests). FIG. 3D: The mean cross-correlation between BOLD and CSF signals shows strong correlations between these signals (n=176 segments, 13 subjects). Shaded blue is standard error across segments; black dashed line is 95% interval of shuffled control distribution. FIG. 3E: The CSF time-series is strongly correlated with the negative derivative of the BOLD signal (derivative amplitude scaled to match), suggesting that CSF flows up the fourth ventricle when blood flows out of the head.

FIG. 4A: The smoothed power envelope of slow (0.2-4 Hz) EEG waves is correlated with the cortical gray matter BOLD signal during sleep, across all subjects (n=13 in sleep; 11 in wake). Shaded region is standard error across segments, black dashed line is 95% confidence intervals of the shuffled distribution using sleep segments. FIG. 4B: EEG slow waves are correlated with the CSF inflow signal (n=13 sleep; 11 wake). Shaded and dashed lines as in panel A. FIG. 4C: Diagram of components included in the model linking neural activity to CSF flow. The EEG signal is used to predict cerebral blood flow (CBF) and cerebral metabolic rate of oxygen (CMRO2). CBF alters cerebral blood volume (CBV), and together these produce the BOLD signal. The CBV changes are in turn used to predict changes in CSF volume and the measured CSF (CSFm) inflow signals. FIG. 4D: Example time-series of the CSF signal prediction using the EEG power envelope. Biophysical modeling of the CSF as resulting from neurally-driven blood flow captures time-varying CSF dynamics. FIG. 4E: The model of CSF dynamics based on the predicting hemodynamic response to EEG signals shows significant predictive value across all sleep segments. This prediction of CSF dynamics from the EEG during sleep was greater than the shuffled control and greater than the wake segments.

FIG. 5A shows an implementation of delayed CBF scenario: the CBF impulse response timing matches the empirical CSF impulse response, corresponding to a slightly slower but still physiological blood flow response, as compared to the fixed-parameter model. FIG. 5B shows an implementation of the delayed CBV scenario: plotting impulse response of the best-fit CBV impulse response (green) when holding the CBF impulse response constant at the fixed parameters, using a viscoelastic time constant of 30 s. This time constant provided the best fit within the physiological range of [0 30] s. The responses of modeled blood flow (yellow) and CSF data (purple) are also shown for comparison.

DETAILED DESCRIPTION

Figures 1A, 1B:
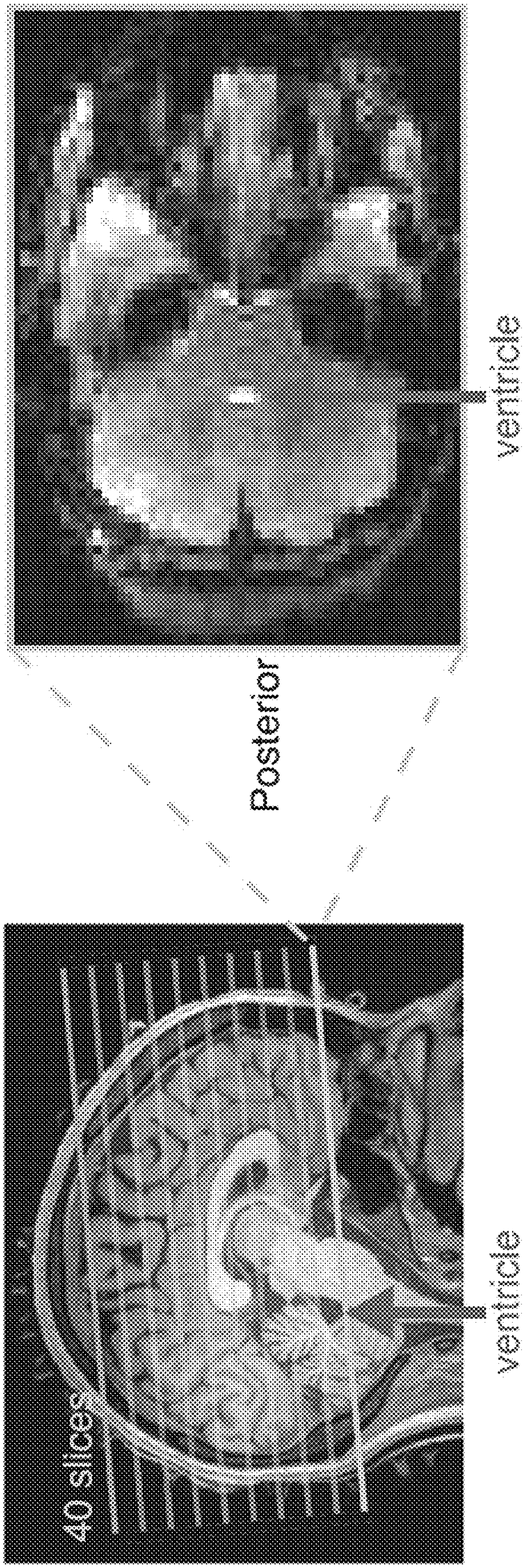
FIGS. 1A-1I show an example of fMRI detecting large oscillations in CSF flow in the fourth ventricle during sleep.

Described here are systems and methods for generating an imaging-based biomarker that indicates a neurological and/or neurovascular state of a subject. The imaging-based biomarker is generated from magnetic resonance imaging data acquired from the subject while the subject was in a sleep state, in an awake state, or during both. These magnetic resonance imaging data are acquired in such a way so that they simultaneously enable measurement of cerebrospinal fluid ("CSF") flow and blood-oxygenation-level dependent ("BOLD") signals. As will be described, the imaging-based biomarker can be generated based on a correlation between CSF signals and BOLD signals extracted from these magnetic resonance imaging data.

The methods described in the present disclosure enable the measurement of oscillating patterns of CSF waves during sleep and/or wakefulness, and how these CSF waves are tightly coupled to neural slow waves during sleep, which drive blood volume and CSF flow oscillations.

Techniques for accelerated neuroimaging with simultaneous EEG can be used to measure physiological and neural dynamics in the human brain. A coherent pattern of oscillating electrophysiological, hemodynamic, and CSF dynamics that appears during non-rapid eye movement (NREM) sleep can be measured and used as an imaging-based biomarker for indicating the neurological and/or neurovascular state of a subject. In this pattern, neural slow waves are followed by waves of CSF. The coupled timing of these oscillations can be modeled using a model in which slow waves of coherent neural activity entrain blood volume changes, which in turn induces pulsatile CSF flow on a macroscopic scale. The cognitive and physiological effects of sleep are linked through this coupled oscillatory neural, vascular, and mechanical origin, thereby providing the imaging-based biomarker that can be used to indicate the neurological and/or neurovascular state of the subject.

As one example, the neurological state of the subject can indicate or otherwise assess neurodegeneration in the subject. As another example, the neurological state of the subject can indicate, guide, or assess the efficacy of a drug treatment delivered to the subject. As still another example, the neurological state of the subject can indicate a sleep disturbance, or a likelihood of a sleep disturbance in the subject. As yet another example, the neurological state of the subject can indicate a neurovascular state of the subject, such as a prediction, estimation, or quantification of vascular disease in the subject.

The methods described in the present disclosure provide advantages relative to other CSF imaging methods. As one example, the methods are multimodal, in that CSF can be measured simultaneously with blood oxygenation. If EEG is also used, then the methods also measure electrophysiological activity. As another example, a method for generating an imaging-based biomarker can be based on either BOLD signals or CSF signals alone. In such examples, the BOLD signals can be used to predict CSF signals and/or the neurological and/or neurovascular state of the subject, or the CSF signals can be used to predict the BOLD signals and/or the neurological and/or neurovascular state of the subject. As still another example, the methods described in the present disclosure can be used to assess the physiological states linked to sleep directly through measurements of localized CSF flow dynamics.

The multimodal data acquisition allows for identification of whether CSF flow is altered in addition to whether its coupling to hemodynamics or neural activity is also altered. As another advantage, the methods can detect if the pulsatile dynamics of CSF flow are altered in real-time, and not just as average rates over long time periods. This rapid acquisition is particularly useful in the multimodal context because it allows for measuring the coupling between CSF waves and hemodynamic waves.

In example studies, during NREM sleep, a significantly large pulsatile oscillation in the CSF signal was observed at 0.05 Hz. This CSF signal was analyzed across all sleep segments, confirming that identified sleep segments exhibited low-frequency EEG signatures of NREM sleep. A 5.52 dB increase in the amplitude of the CSF signal was observed, peaking at 0.05 Hz during sleep (95% confidence interval (CI)=[2.33 7.67]; p=0.003, signed-rank test), suggesting that large waves of CSF inflow occur approximately every 20 seconds.

Figures 1C, 1D, 1E:
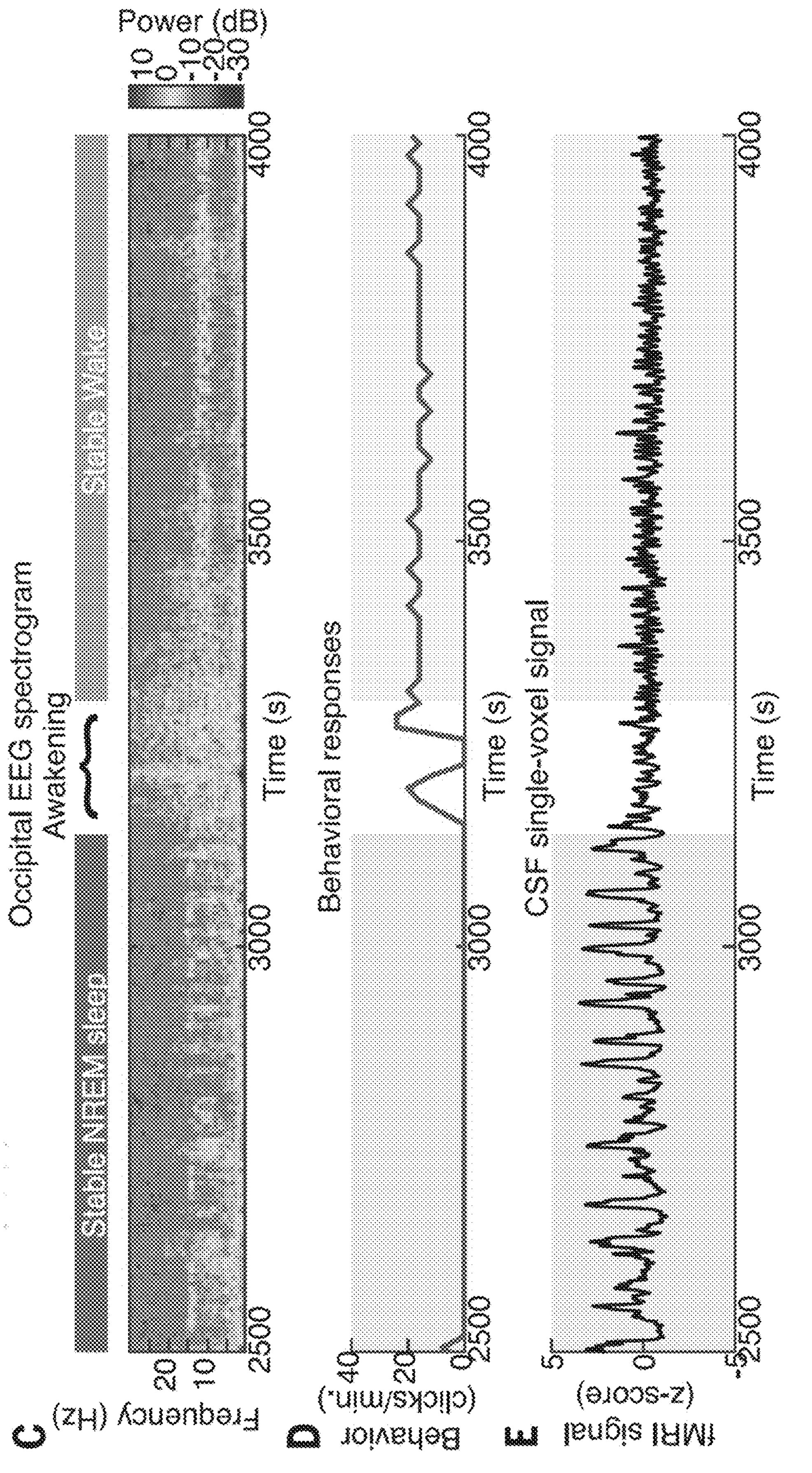
Figure 1F:
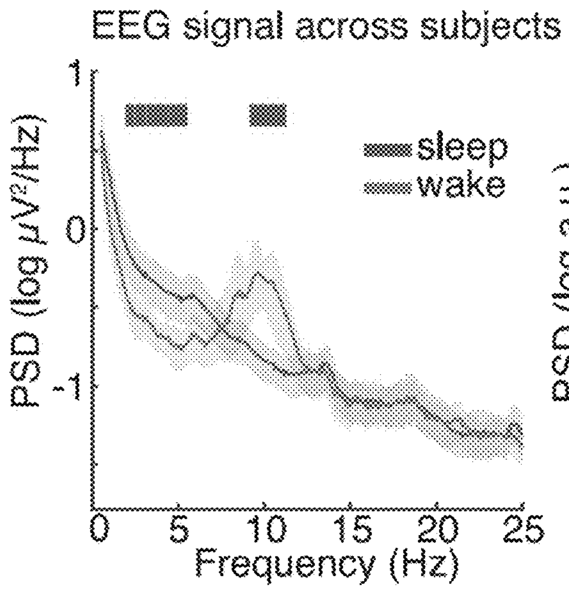
Figure 1G:
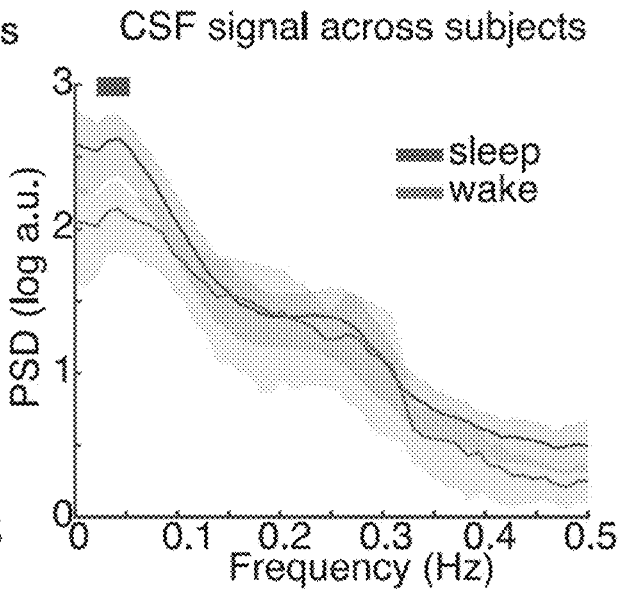
Figure 1H:
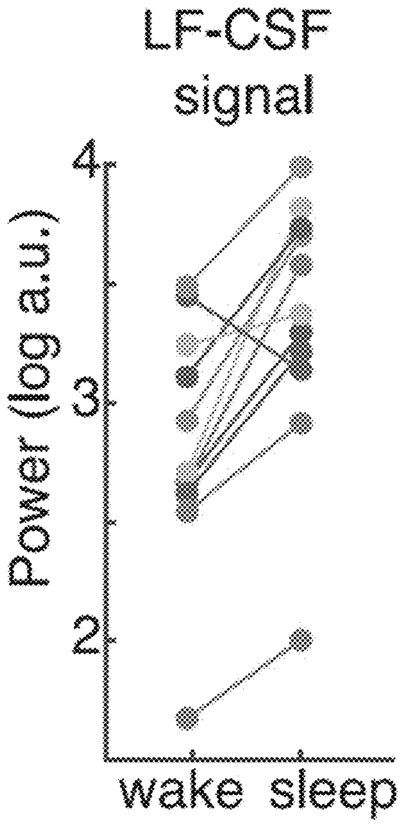
Figure 1I:
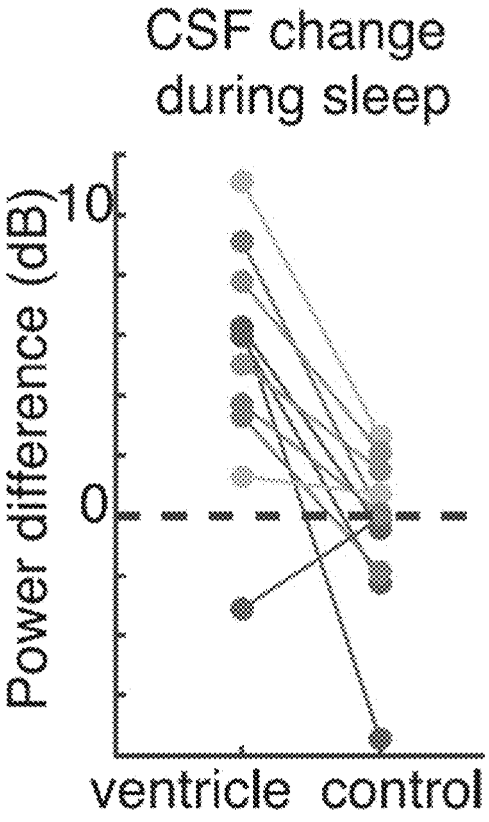

FIGS. 1A-1I depict an example of fMRI detecting large oscillations in CSF flow in the fourth ventricle during sleep. FIG. 1A shows an example scan positioning in one subject, in which the yellow box overlay shows the position of the functional acquisition volume relative to the anatomical image. The bottom of the functional acquisition intersects with the fourth ventricle (red arrow), allowing inflow to be measured as bright signal in these lower slices. FIG. 1B shows an example image from the bottom slice of the functional volume. The inflow through the ventricle is detected as a bright signal (red arrow). FIG. 1C is an EEG spectrogram from this subject, and shows stable periods of NREM sleep and wake (signaled by the ~10 Hz occipital alpha rhythm during wake). FIG. 1D shows an example behavioral task performance in this subject, which confirms sleep/wake segmentation. FIG. 1E depicts a time-series of a single voxel in the ventricle (temporally smoothed with 10-TR kernel), and shows large slow pulsatile dynamics in sleep that subside during the wake period, which exhibits a smaller and faster rhythm synchronized to respiration. FIG. 1F shows occipital EEG across wake vs. sleep segments, and confirms high delta power in sleep, as opposed to high alpha power in wake. The shaded region is 95% CIs; red lines mark non-overlapping CIs. FIG. 1G shows a spectrum of ventricle signal across all subjects scanned at 3T, which shows increased 0.05 Hz power during sleep. The shaded region is 95% CIs; red lines and star mark non-overlapping CIs. FIG. 1H shows that low-frequency power in the ventricle increased during sleep, and FIG. 1I shows that this sleep-selective power increase was specific to the ventricle and not observed in a neighboring cerebellar ROI positioned on the same edge slices.

Figures 2A, 2B, 2C:
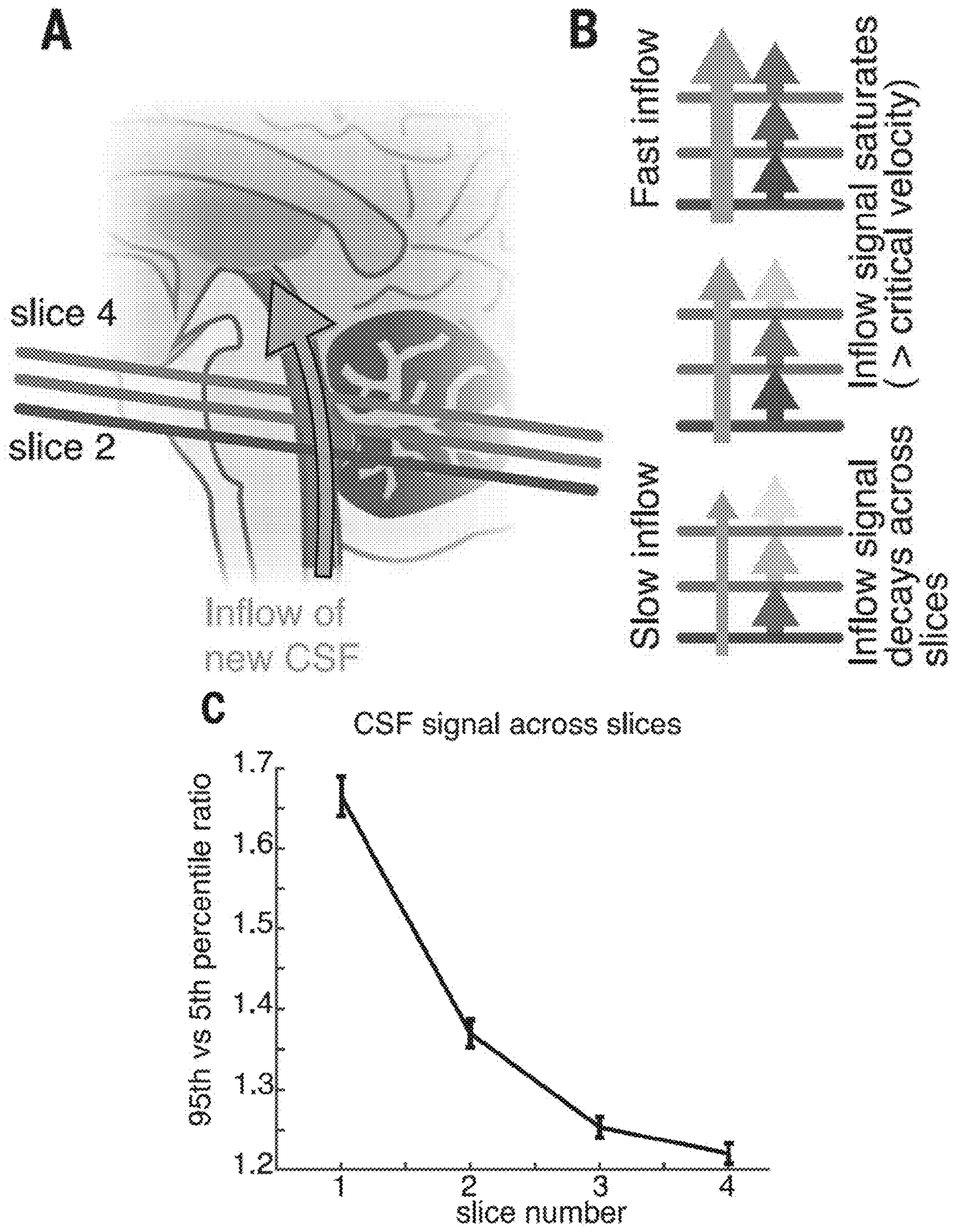
FIGS. 2A-2D show an example of ventricle signals corresponding to a 0.05 Hz pulsatile inflow of CSF.

Because inflow signals are caused by fresh magnetized fluid flowing into the acquisition volume, the observed signal caused by CSF flow should be brightest in slices near the edge of the imaging volume, and decay as it passes into more medial slices (FIGS. 2A, 2B). Consistent with this prediction, a gradient of signal amplitudes across the slices can be observed (FIGS. 2C, 2D), with the bottom slice exhibiting the largest and earliest response. Some large inflow events may exhibit matched amplitudes across the first few slices (FIG. 2D), suggesting the CSF flow velocity exceeded the critical velocity of the imaging acquisition ($v_c$=6.8 mm/s), leading to equally bright signals beyond the entry slice. Together, these data identified a pattern of large-amplitude pulsatile flow of CSF at 0.05 Hz that appears during NREM sleep.

Figure 2D:
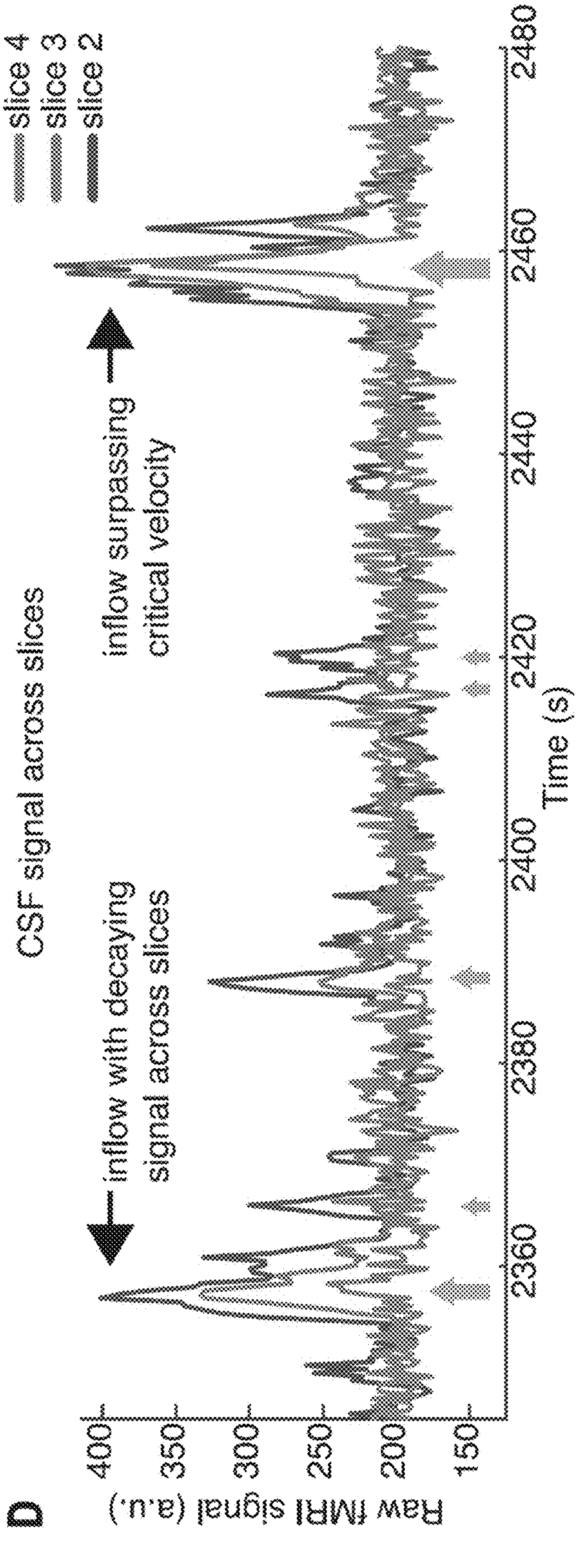

FIG. 2A shows a schematic of a data acquisition in which new CSF flowing into the imaging volume will generate bright signals. FIG. 2B shows an example of inflow signals that will be largest in the bottom slice, and decrease in amplitude inwards. If flow exceeds the critical velocity, then CSF in the bottom slice is completely replaced and signal amplitudes are large in inner slices as well. FIG. 2C shows that mean amplitude across slices decays in ascending slices. Error bars are standard error across all segments with the ROI present in four contiguous slices. FIG. 2D shows an example time-series from the bottom slices of the imaging volume in the fourth ventricle, which demonstrates largest and earliest signal in the lower (e.g., second) slices and smaller signals in higher (e.g., fourth) slices, consistent with a pattern of CSF inflow. Orange arrows point out inflow events of varying amplitude: lower flow velocities lead to signals that decay in upper slices, whereas higher flow velocities can cause maximum signal to be reached in the inner slices as well.

It was observed that these slow macroscopic CSF oscillations are linked to slow hemodynamics at the macro scale. In an example study, an increase in BOLD signal amplitude was measured in the cortical gray matter fMRI signal during sleep (mean increase=3.28 dB; CI=[0.09 6.54]; p=0.032, signed-rank test). It was discovered that the CSF signal is tightly temporally coupled to the cortical gray matter BOLD oscillation during sleep. Cross-correlating the two signals indicates that gray matter BOLD and CSF are anticorrelated (max R=−0.48 at lag=2s, p<0.001, shuffling).

This anticorrelation suggests an alternation of blood flow and CSF flow into the brain during sleep, as BOLD signal increases are typically driven by increased blood flow with subsequent increases in blood volume. These BOLD signal oscillations corresponded to an oscillation in cerebral blood volume, such that as blood volume decreases there is a corresponding inflow of CSF. This pattern reflects a displacement effect, where due to constant intracranial volume, more CSF flows in when less volume is occupied by the blood. Based on this, CSF inflow can approximately match the negative of the derivative of the BOLD oscillation, which in some instances may be the low-frequency (e.g., less than 0.1 Hz) BOLD oscillation, which when only inflow and not outflow is measured, can be thresholded at zero. In an example study, comparing the CSF time-series to the derivative signal showed high correspondence (max R=0.59 at lag −1.8 s; zero-lag R=0.49, p<0.001, shuffling).

Figure 3A:
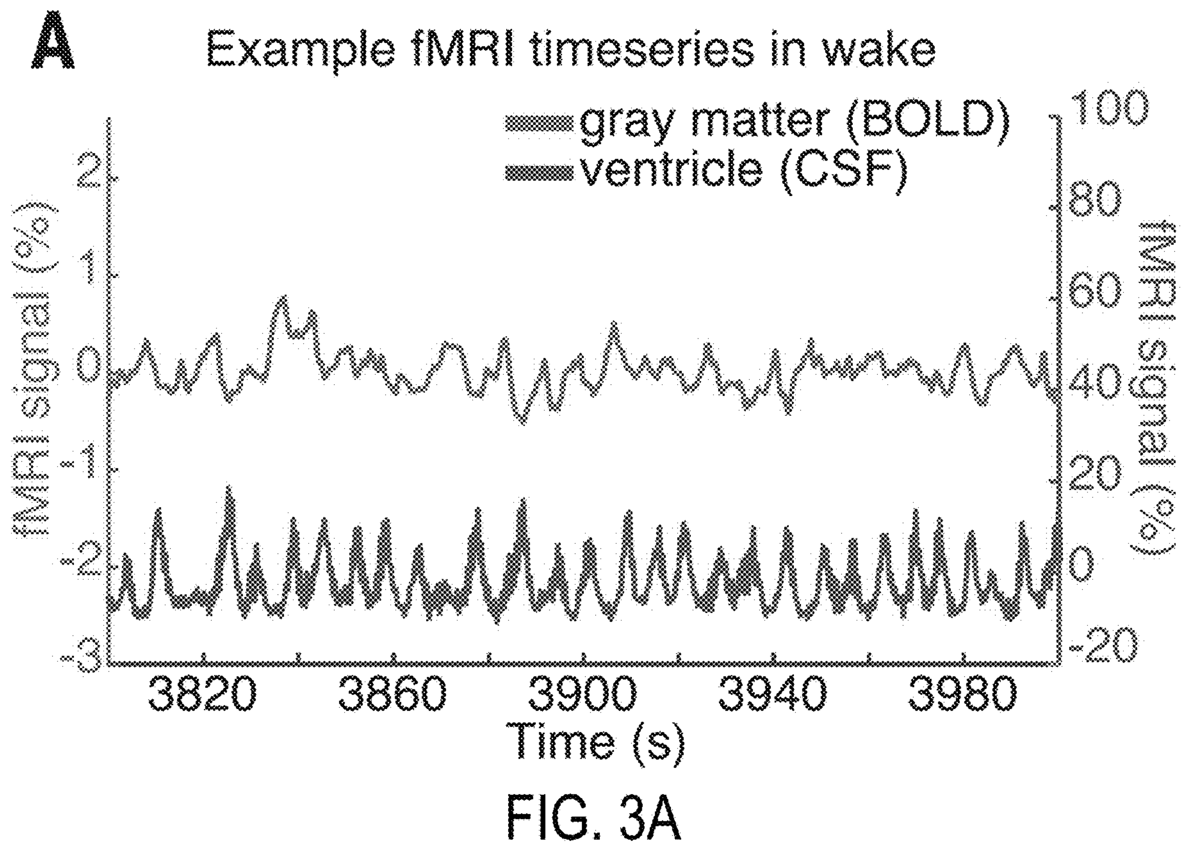
FIGS. 3A-3E show an example of how cortical gray matter exhibits a large-amplitude hemodynamic oscillation during sleep that is anticorrelated to CSF flow.
Figure 3B:
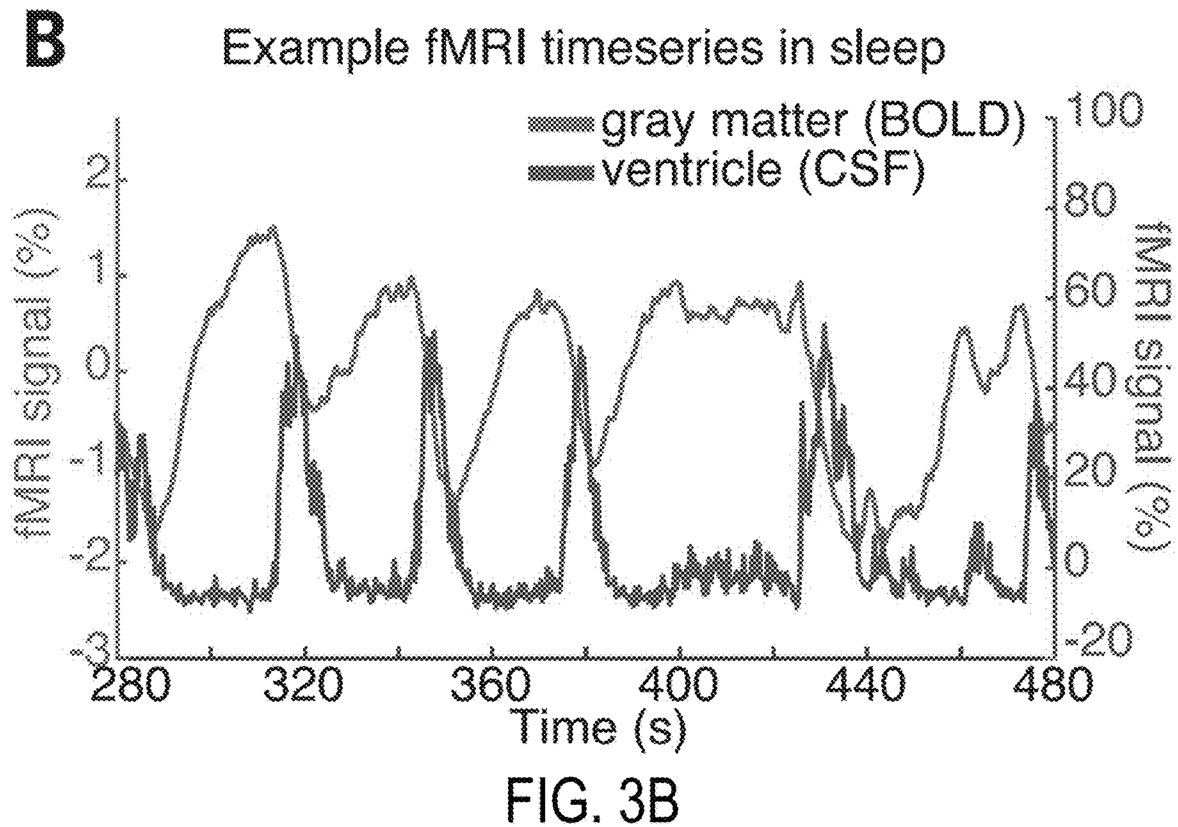
Figures 3C, 3D, 3E:
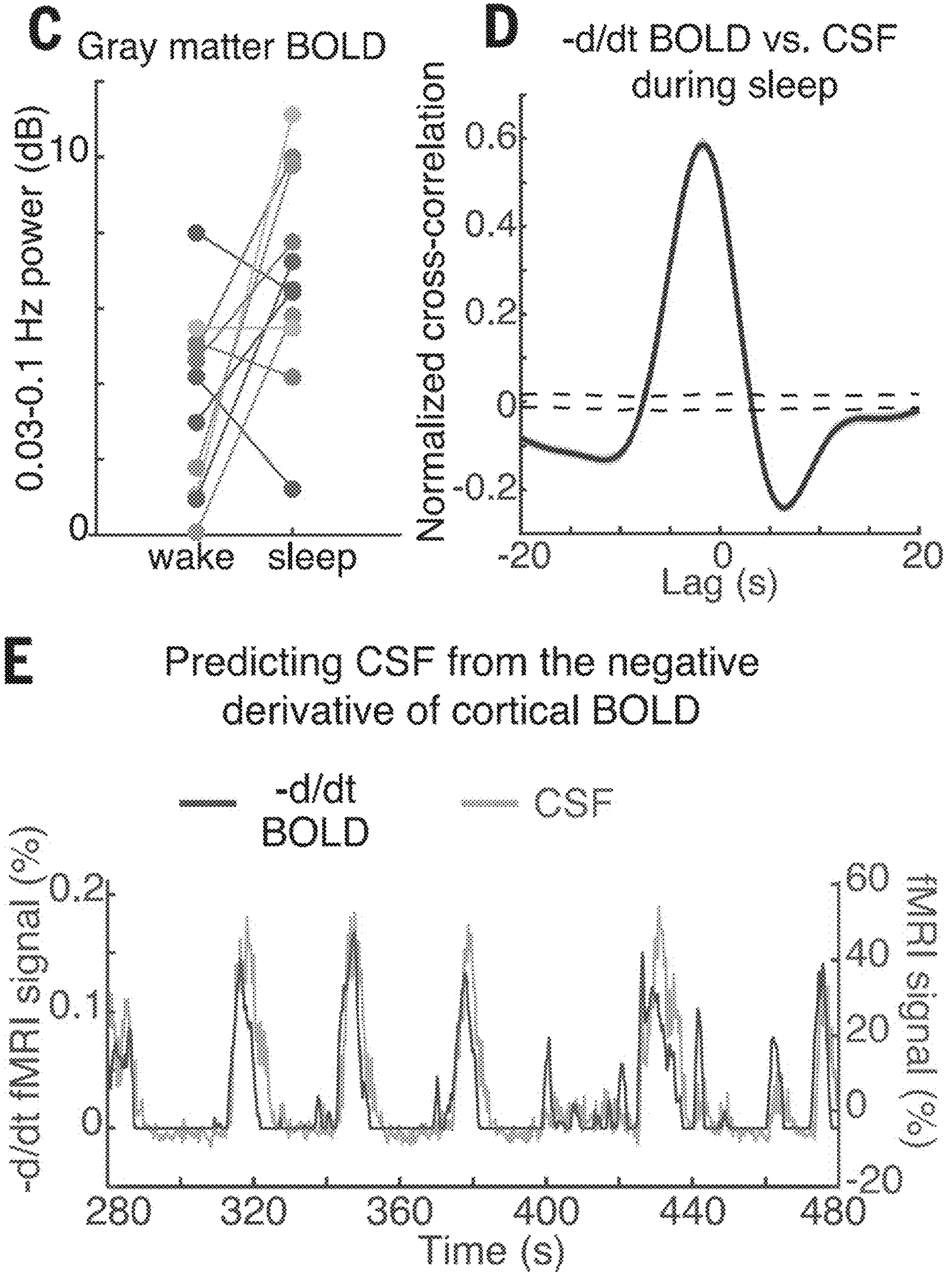

FIGS. 3A-3E show an example of how cortical gray matter exhibits a large-amplitude hemodynamic oscillation during sleep that is anticorrelated to CSF flow. FIG. 3A shows an example fMRI time-series of the mean BOLD signal across all cortical gray matter, and the mean ventricle signal, from one subject scanned at 3T. During wake, gray matter BOLD and ventricle CSF signals are low-amplitude. FIG. 3B shows that during sleep, a large-amplitude BOLD oscillation appears, and its time-course is coupled to the ventricle CSF signal (~0.05 Hz). FIG. 3C shows that the mean cortical gray matter BOLD signal power across subjects increases during sleep (n=11 subjects for pairwise tests). FIG. 3D shows that the mean cross-correlation between BOLD and CSF signals shows strong correlations between these signals (n=176 segments, 13 subjects). Shaded blue is standard error across segments; black dashed line is 95% interval of shuffled control distribution. FIG. 3E shows that the CSF time-series is strongly correlated with the negative derivative of the BOLD signal (derivative amplitude scaled to match), suggesting that CSF flows up the fourth ventricle when blood flows out of the head.

Figures 4A, 4B, 4C, 4D, 4E:
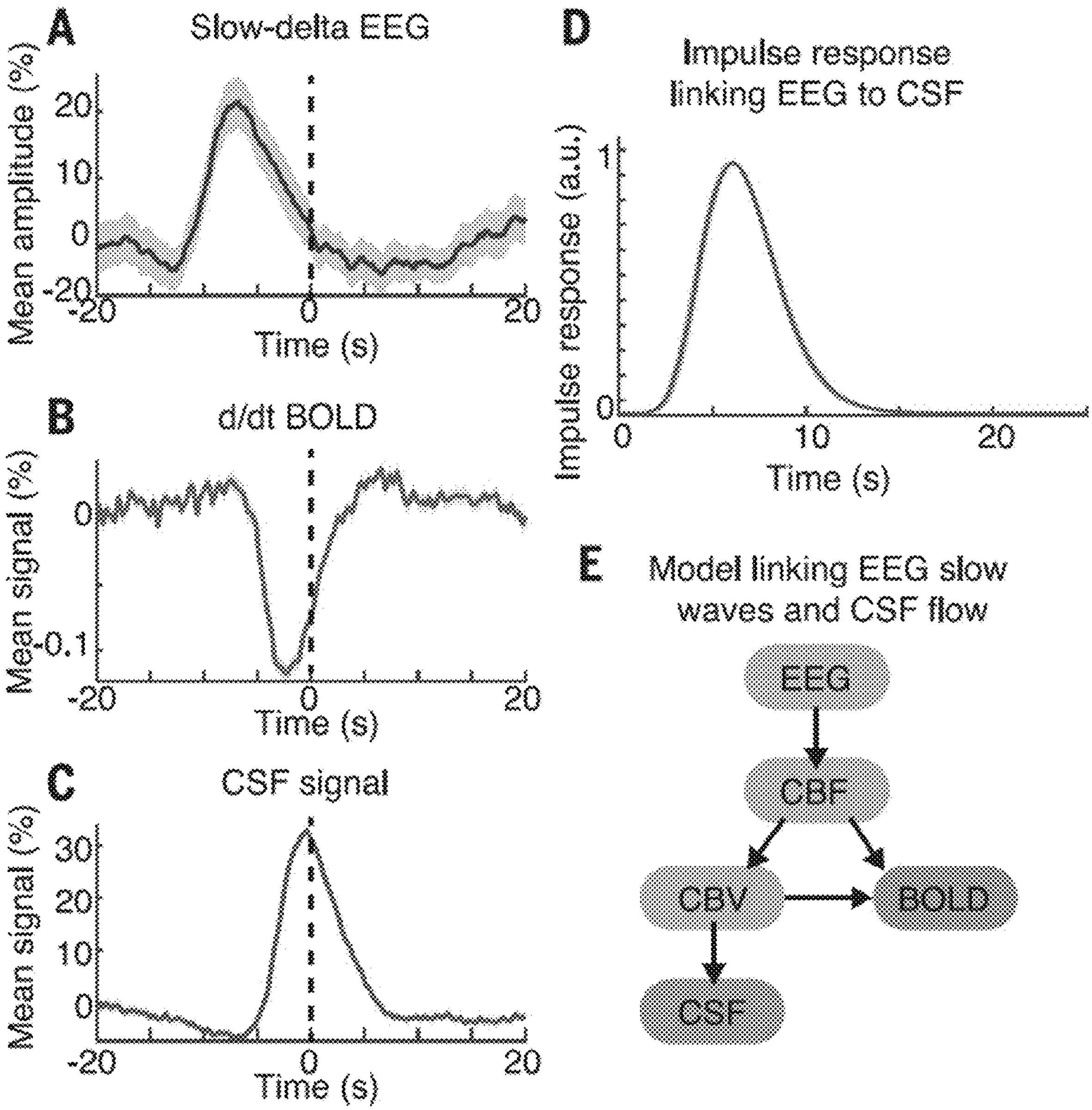
FIG. 4A-4E show the slow waves in the EEG are coupled to BOLD and CSF oscillations, consistent with a model in which coherent neural activity entrains oscillations in blood volume and CSF.

It is contemplated that large, slow-delta (0.2-4 Hz) electrophysiologic oscillations characteristic of NREM sleep can lead to these large coherent BOLD and CSF oscillations. Specifically, as the activity of large-scale neuronal ensembles fluctuates during NREM sleep, this fluctuation may drive oscillatory dynamics in oxygen-rich blood flow, and in turn displacement effects driving CSF flow. Coupling between EEG amplitude and the BOLD oscillations can be measured (max R=−0.15 at lag=−7.2 s; p<0.001, shuffling), suggesting that neural activity entrained the large-amplitude hemodynamic signals seen during sleep (FIG. 4A). In turn, the EEG slow oscillations were also correlated with the CSF flow signal (FIG. 4B; max R=0.15 at lag=−4.2 s; p<0.001, shuffling). These results suggest that the large BOLD and CSF flow oscillations during sleep are coupled to coherent slow oscillations in neural electrophysiological activity during sleep.

Together, these results demonstrated interlinked oscillations in neural EEG activity, BOLD hemodynamics, and CSF flow, and suggested a potential mechanism: the increasing coherence of large, slow oscillations in neural activity that occurs during sleep may entrain oscillations in cerebral blood volume, and in turn exert a displacement effect leading to changes in CSF flow rates. To explicitly analyze this mechanism, a model of the predicted blood volume and CSF changes over time can be constructed (FIG. 4C) and used to predict these signals from biophysically plausible dynamics. For example, the model can be constructed to simulate how blood volume and BOLD dynamics change due to neural activity in addition to modeling CSF inflow.

As an example, the power envelope of EEG slow oscillations can be extracted and used to predict causing a negative BOLD signal due to their associated suppression of neural activity. This neural oscillation can then be used to predict the time-course of blood flow, and the subsequent BOLD signal can be calculated. The CSF flow can then modeled as the negative of the normalized CBF. Using physiologically plausible parameters with no additional parameter fitting, such a model can be used to predict the dynamics of the CSF time-series using only information from the EEG slow-delta (0.2-4 Hz) waves (FIG. 4D, maximal R=0.22 at lag=1 s; CI across segments=[0.17 0.27]; p<0.001, shuffling).

This constructed model suggests a specific sequence of events: the neural slow wave is followed by a reduction in CBF that in turn leads to CSF inflow at a lag of about 4 seconds, and subsequent suppression of BOLD signals peaking at a lag of about 6 seconds (due to reduced CBF). This model therefore demonstrates that physiologically plausible coupling between neural activity, blood flow, and CSF flow can produce the observed interlinked dynamics during sleep.

Thus, sleep is associated with large coupled oscillations in neuronal activity, blood oxygenation, and CSF flow in the human brain. In some instances, the low-frequency oscillations in two or more of these physiological sources can be coupled. The phase of the CSF and hemodynamic signals is entrained to slow oscillatory EEG dynamics, suggesting direct interaction of the physiological and neural rhythms that appear during sleep. While electrophysiological slow waves are well known to play important roles in memory consolidation and neural processing, they can also be used to indicate contributions to the physiologically restorative effects of sleep, as large-scale coherent neural activity may drive brain-wide pulsations in blood volume and CSF flow.

The physiological models described in the present disclosure address a missing link in the neurophysiology of sleep. Macroscopic changes in CSF flow are expected to alter glymphatic clearance, as pulsatile dynamics can increase mixing and diffusion of fluids and clearance from brain tissue. Neurovascular coupling has been proposed to drive glymphatic clearance, but because sleep is associated with suppressed neural activity it was previously no know why it would cause larger vascular pulsations and higher clearance rates. It is a discovery of the present disclosure that slow neural and hemodynamic oscillations can drive this process. The widespread coherence and low-frequency nature of neural activity during sleep can be associated with coupled oscillations in macroscopic hemodynamics and CSF flow, identifying a mechanical bridge between the EEG and physiological effects of sleep.

The identification of sleep-associated CSF fluid dynamics also suggests a new biomarker to be explored in clinical conditions associated with aggregate proteins and sleep disturbance, such as Alzheimer's disease. Memory impairment in aging is associated with suppressed slow waves; the models described in the present disclosure suggest this slow wave loss would in turn lead to decreased CSF flow. Furthermore, the methods described in the present disclosure hint at a potential bridge between findings that tau CSF levels and amyloid beta depend on sleep and neural activity and that oscillatory neural activity leads to reduced tau. Coherent neural activity may directly drive hemodynamic and CSF oscillations and thus contribute to aggregate clearance through fluid exchange. Pulsatile CSF flow can therefore be measured during sleep, and because slow rhythms in neural activity are interlinked with CSF flow, hemodynamic oscillations can provide an intermediate mechanism through which these two processes are coupled. An example schematic view of a physiological model is shown in FIG. 4E.

In one example physiological model, the blood flow response to neural activity can be calculated as:

$$f(t) = -n * h(t); \tag{1}$$

where f(t) is the relative cerebral blood flow ("CBF"), which is always positive and is normalized to a value of 1; n is the power envelope of the EEG signal between 0.2 Hz and 4 Hz; and h(t) is the flow impulse response to neural activity, which can be modeled as the gamma distribution:

$$h(t) = \frac{(t/\tau_f)^{(z-1)}\exp(-t/\tau_f)}{\tau_f(z-1)!}. \tag{2}$$

The value for $\tau_f$ can be set at 2.1, and z can be set at 3.

A term for CSF is added to this model, such that a decrease in blood volume will elicit an increase in CSF volume. CSF flow can be approximated as the opposite of the cerebral blood flow:

$$CSF = -f(t) + 1. \tag{3}$$

This model simplifies the relationship between blood and CSF by assuming that blood flow and CSF flow changes are exactly coupled, and assuming that net CSF flow is zero. The CSF term thus includes an offset of 1, as CSF flow can be negative or positive, and is centered at zero. In contrast, the CBF f(t) term is always positive, representing inflow of fully oxygenated blood, and is normalized to 1. The cross-correlation between this CSF prediction and the CSF signal was then calculated.

As another example of a physiological model, numerical optimization can be used to examine the best-fit impulse response between EEG and CSF. The shape and scale parameters of a gamma distribution can first be fit, using as the cost function the root-mean-squared error between the CSF prediction and the true CSF signal. This process can be used to generate the EEG-CSF impulse response, as shown in FIG. 4D.

To compare the best-fit impulse response for EEG-CSF to the model predictions of CBF and cerebral blood volume ("CBV"), the CBF equations as described above can be used, and the predicted CBV change can be calculated using a balloon model:

$$\frac{dv}{dt} = \frac{1}{\tau_{MTT}}(f(t) - f_{out}(v, t)); \tag{4}$$

$$f_{out}(v, t) = v^{1/\alpha} + \tau_v \frac{dv}{dt}. \tag{5}$$

As an example, the physiological parameters can be fixed at $\tau_{MTT}$=4, $E_0$=0.4, α=0.4. To find the best fit delay between flow and volume, either the CBF parameters (e.g., $\tau_f$ and z) or the viscoelastic time constant, $\tau_v$, can be varied, such as in a range between 0 and 30. The model fitting minimized the difference between the derivative of CBV and the inverse of CSF flow.

Figure 5A:
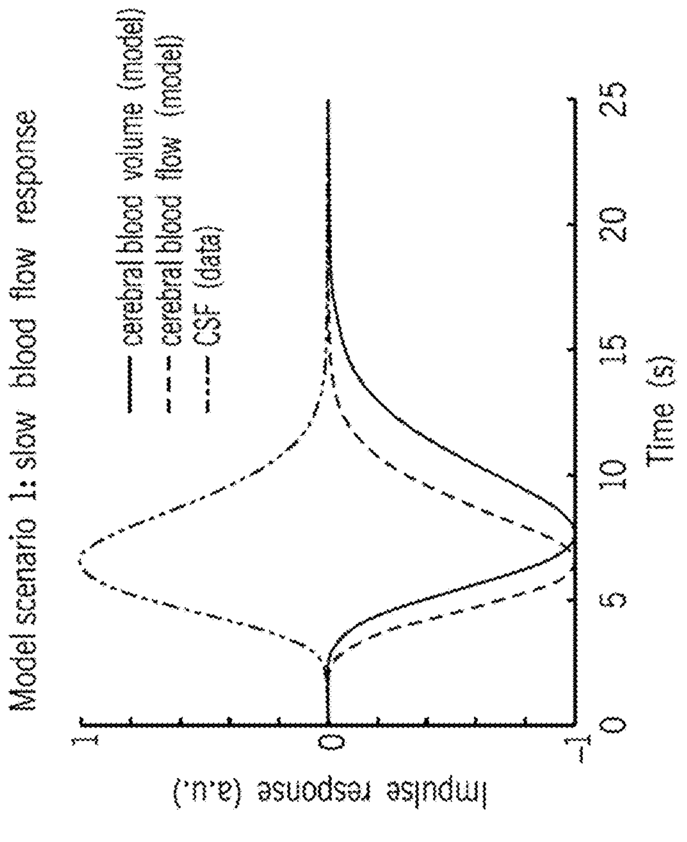
FIGS. 5A and 5B show an example of best fit impulse response for the CSF dynamics, consistent with a biophysical model of cerebral blood volume dynamics. The numerically fit CSF impulse response shows a similar, but slightly slower waveform, as compared to the fixed-parameter CBF impulse response, reflecting the ability of CSF measures to directly correspond to broader physiological changes.
Figure 5B:
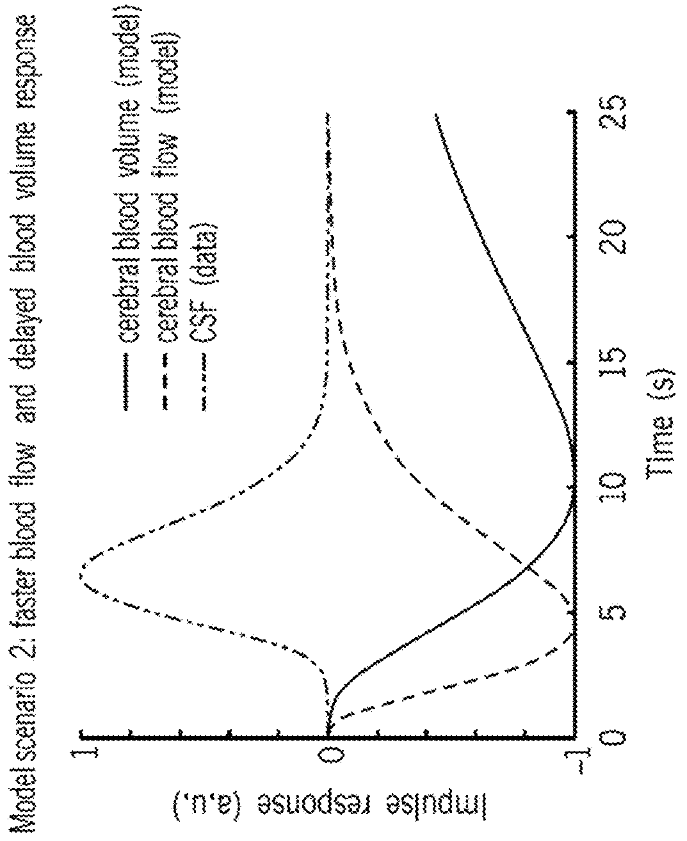

FIGS. 5A and 5B show an example of best fit impulse response for the CSF dynamics, consistent with a biophysical model of cerebral blood volume dynamics. The numerically fit CSF impulse response shows a similar, but slightly slower waveform, as compared to the fixed-parameter CBF impulse response. FIGS. 5A and 5B demonstrate two model scenarios that are consistent with this CSF impulse response. First, this impulse response timing is within the established physiological range for CBF responses, so this result would be consistent with a slightly slower CBF coupling to spontaneous slow-delta EEG in sleep (as compared to task-induced fMRI measurements). Alternatively, it could reflect delayed changes in blood volume relative to blood flow.

FIG. 5A shows an implementation of delayed CBF scenario: the CBF impulse response timing matches the empirical CSF impulse response, corresponding to a slightly slower but still physiological blood flow response, as compared to the fixed-parameter model. FIG. 5B shows an implementation of the delayed CBV scenario: plotting impulse response of the best-fit CBV impulse response (green) when holding the CBF impulse response constant at the fixed parameters, using a viscoelastic time constant of 30 s. This time constant provided the best fit within the physiological range of [0 30] s. The responses of modeled blood flow (yellow) and CSF data (purple) are also shown for comparison.

Figure 6:
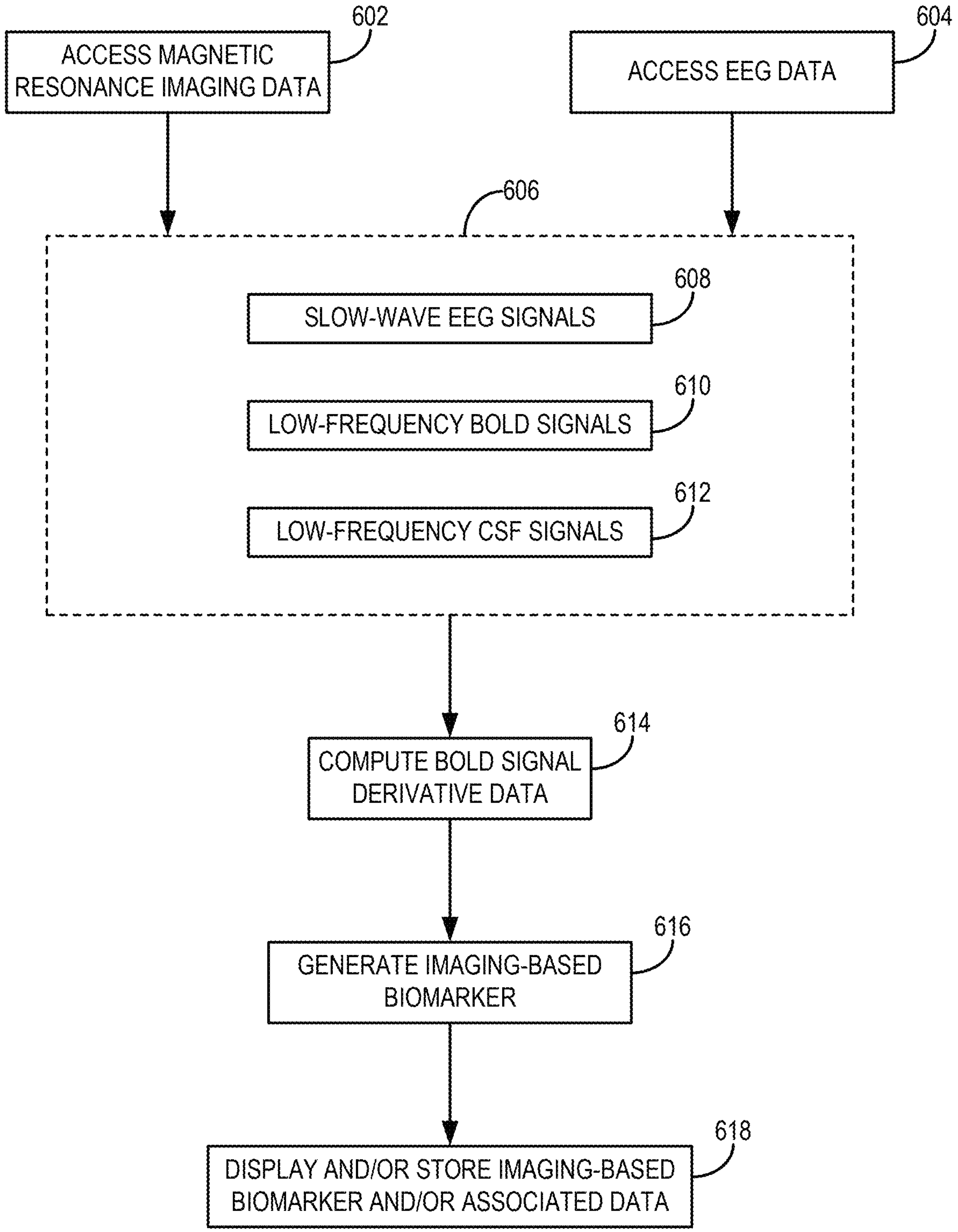
FIG. 6 is a flowchart setting forth the steps of an example method for generating an imaging-based biomarker indicating a neurological state of a subject, according to some embodiments described in the present disclosure.

Referring now to FIG. 6, a flowchart is illustrated as setting forth the steps of an example method for generating an imaging-based biomarker that indicates a neurological and/or neurovascular state of a subject based on a comparison between BOLD signals and CSF signals measured in the subject using magnetic resonance imaging.

The method includes accessing magnetic resonance imaging data with a computer system, as indicated at step 602.

Accessing the magnetic resonance imaging may include retrieving such data from a memory or other suitable data storage device or medium. Alternatively, accessing the magnetic resonance imaging may include acquiring such data with an MRI system and transferring or otherwise communicating the data to the computer system, which may be a part of the MRI system.

In general, the magnetic resonance imaging data can include data (e.g., k-space data) and/or images acquired with an MRI system. The magnetic resonance imaging data are acquired from a subject's brain. Further, the magnetic resonance imaging data can be acquired while the subject is in a sleep state or a wake state. In some instances, the magnetic resonance imaging data are acquired during both a sleep state and a wake state. By placing the edge of the acquisition volume at a region containing CSF, such as a ventricle (which in some non-limiting examples may be the fourth ventricle) or aqueduct, simultaneous measurement of CSF inflow signals and BOLD dynamics can be achieved.

As one example, the magnetic resonance imaging data can include both functional imaging data and anatomical imaging data. For instance, the magnetic resonance imaging data can be acquired using a multi-echo MPRAGE sequence, and in some instances can include acquiring data with isotropic resolution (e.g., 1 mm isotropic resolution). The anatomical data can assist with identifying the CSF spaces, such as ventricles, near which the functional data should be acquired.

Functional data can be acquired over an imaging volume (e.g., 40 slices) with isotropic resolution (e.g., 2.5 $mm^3$ isotropic voxels). Such an acquisition volume can cover most of the brain, or a smaller part of the brain. fMRI scanning can include a single-shot gradient echo SMS-EPI sequence with MultiBand factor=8, matrix=92×92, blipped CAIPI shift=4, TR=367 ms, nominal echo-spacing=0.53 ms, flip angle=32-37, no in-plane acceleration. To achieve high temporal resolution imaging, accelerated data acquisition techniques can be used to acquire data at fast rates (e.g., TR <800 ms).

The method may also include accessing electroencephalography ("EEG") data with the computer system, as indicated at step 604. Accessing the EEG may include retrieving such data from a memory or other suitable data storage device or medium. Alternatively, accessing the EEG may include acquiring such data with an EEG system and transferring or otherwise communicating the data to the computer system, which may be a part of the EEG system. In some embodiments, the EEG data are acquired contemporaneously with the magnetic resonance imaging data.

As one example, EEG data can be acquired using an MR-compatible EEG system, which may include geodesic nets (e.g., 256-channel geodesic nets) and an amplifier operating at a sampling rate of 1000 Hz. EEG acquisition can be synchronized to the MRI scanner 10 MHz clock to reduce aliasing of high-frequency gradient artifacts. The scanner cryopump can be shut off during EEG acquisition to reduce vibrational artifacts, or vibrations can be removed during post-processing.

Reference signals to be used for EEG noise removal can be acquired using a reference layer cap composed of an isolating vinyl layer and conductive satin layer on the head, with grommets inserted to allow electrodes to pass through. In addition to the electrodes passing through the grommets, 6-8 electrodes on the forehead also made contact with the scalp, for a total of 30-32 EEG electrodes per subject. Physiological signals can be simultaneously acquired.

ECG signals can also be measured through two disposable electrodes placed on the chest diagonally across the heart, with an MR-compatible lead. Respiration can also be measured, such as through a piezoelectric belt around the subject's chest.

Various signal data are then extracted from the magnetic resonance imaging data and the EEG data, as indicated at process block 606. As shown, the extracted signal data generally can include slow-wave EEG signals extracted from the EEG data, as indicated at 608; BOLD signals extracted from the magnetic resonance imaging data, as indicated at 610; and CSF signals extracted from the magnetic resonance imaging data, as indicated at 612.

In some embodiments, stable wake periods, stable sleep periods, or both can be identified and signal extracted only from those data acquired during the respective stable periods. For instance, the BOLD signals and/or CSF signals can be extracted from those magnetic resonance imaging data acquired during the identified stable wake periods, stable sleep periods, or both.

The sleep and wake segment identification can be based on examining ongoing dynamics in the EEG spectrograms, based on analysis of the magnetic resonance imaging data, or by performing conventional sleep scoring in discrete windows.

As one example, continuous sleep and wake segments can be selected based on occipital EEG spectrograms (e.g., from the channel nearest to OZ with good recording quality). EEG signatures of sleep included loss of occipital alpha (8-12 Hz) rhythms and increased delta (0.5-4 Hz) and theta (4-8 Hz) power. The occipital EEG channel can be selected both to provide the ability to identify disappearance of occipital alpha rhythms at sleep onset, allowing for clear segmentation of wake and sleep, and because occipital EEG has the highest signal quality in the MRI environment. As one non-limiting example, periods of at least 90 seconds of low motion and either stable wake or NREM can be identified and extracted for further analysis.

As another example, continuous sleep and wake segments can be selected based on subject behavior and/or translational motion, rotational motion, or both, estimated from the magnetic resonance imaging data. To track behavioral state, a subject can be asked to perform a task (e.g., press a button with every breath) to generate a behavioral response without requiring an external sensory stimulus that might disrupt sleep. Periods of sleep, which as a non-limiting example can be defined through loss of occipital alpha (8-12 Hz) rhythms and increased delta (0.5-4 Hz) and theta (4-8 Hz) power, and failure to perform the behavioral task can then be monitored.

Regarding the slow-wave EEG signals extracted at step 608, the EEG data can be processed to remove artifacts and/or filtered before extracting signals associated with slow-wave EEG signals.

As one example, gradient artifacts can be removed through average artifact subtraction using a moving average of the EEG data acquired within a previous number of repetition time ("TR") periods during which the corresponding magnetic resonance imaging data were acquired. For instance, the number of TRs may be the previous 20 TRs. Electrodes can be re-referenced to this common average, computing this separately for electrodes contacting the head, and those placed on a reference layer. In some instances, channels on the cheeks and borders of a reference cap can be excluded from the common average.

As another example, ballistocardiogram artifacts can be removed using a regression of reference signals from isolated EEG electrodes. When there are a large number of noise electrodes as compared to signal electrodes, the regression can be performed after subsampling the noise electrodes (e.g., using only every fourth isolated electrode). Because the position and physiological noise influences on the electrodes can vary over long recording times, a dynamic time-varying regression of the reference signals can be implemented.

As another example, the EEG data can be filtered, such as by using a bandpass filter to remove unwanted frequency content while retaining the desired frequency content. For instance, the EEG data could be filtered using a bandpass filter having a passband of 0.2-4 Hz. As another example, the EEG data could be filtered into the 0.2-4 Hz band using a finite impulse response filter. In other implementations, a frequency band other than 0.2-4 Hz could also be used, such as 0.2-1 Hz or otherwise.

In some instances, the slow-wave EEG signal amplitudes can be extracted as the magnitude of the Hilbert transform, which can be smoothed, such as by using a moving average of 4 s. When extracting the slow-wave EEG signals, beta values for a best fit regression within sliding time windows can be fit using least-squares or another suitable regression technique. The sliding time windows can have a duration of 30 seconds, as one example, but other sliding window durations can also be used. In still other instances, sliding time windows do not need to be used. The beta values can then be linearly interpolated over the non-overlapping windows. The resulting interpolated beta at every time point can then be used for a local subtraction of the reference signals from the modeled EEG recording. This regression can be performed individually for each EEG channel.

The slow-wave EEG signals, which may be slow-delta EEG envelope data, can then be output by displaying and/or storing the slow-wave EEG signals in a memory or other suitable data storage device or medium.

Regarding the BOLD signals extracted at step 610, the magnetic resonance imaging data can be processed (e.g., to correct for subject motion and reduce noise), one or more regions-of-interest ("ROIs") containing gray matter can be identified, magnetic resonance signals in the gray matter ROI(s) can be further processed (e.g., via detrending and filtering), and the extracted BOLD signals output.

As one example, the magnetic resonance imaging data can be slice timing corrected and motion corrected. Physiological noise removal can also be performed, such as by using a dynamic regression based. For instance, a respiratory trace can be bandpass filtered between 0.16-0.4 Hz using a finite impulse response filter and the instantaneous phase computed as the angle of the Hilbert transform. Cardiac peaks can be detected automatically and the phase modeled as varying linearly between each identified peak. Sine and cosine basis functions using the phase of the signal and its second harmonic can be generated as regressors for physiological noise. This regression can performed over sliding windows (e.g., 1000 second windows sliding every 400 seconds) to enable high-quality physiological noise removal as the heart rate and respiratory rate varied throughout the scan.

Gray matter containing ROI(s) can be defined manually, semi-automatically, or automatically. As one example, the gray matter ROI(s) can be defined using an automated segmentation generated on anatomical images contained in the magnetic resonance imaging data and then registered to the functional images contained in the magnetic resonance imaging data. As another example, one or more ROIs containing other tissues, such as white matter, can be defined using the anatomical imaging data.

In some implementations, the signals in the ROI(s) can then be low-pass filtered to extract the low-frequency signals, generating output as low-frequency BOLD signal data. The signals can be low-pass filtered to retain signals below a cutoff frequency selected from the range of 0.1 Hz to 5 Hz. For instance, the signals can be low-pass filtered below 0.1 Hz. As another example, the signals can be low-pass filtered below 1 Hz, or any other suitable frequency selected from the range of 0.1 Hz to 5 Hz. The BOLD signals, which in some instances may be low-frequency BOLD signals, can then be output by displaying and/or storing the BOLD signals in a memory or other suitable data storage device or medium.

Regarding the CSF signals extracted at step 612, the magnetic resonance imaging data can be processed to identify one or more ROIs, magnetic resonance signals in the ventricle ROI(s) can be further processed (e.g., via detrending and filtering), and the extracted CSF signals can be output.

As described above, because the analysis of CSF dynamics can be performed on non-motion-corrected data (e.g., to measure signal at the edge slices) and long continuous epochs (e.g., to analyze continuous dynamics, which in some instances may be continuous low-frequency dynamics), the analysis can in some instances be performed on magnetic resonance imaging data acquired during periods of stable wake or sleep with low motion. Additionally or alternatively, to enable the analysis of dynamics in a continuous manner, the analysis can extract long segments of stable continuous NREM sleep or wake (no REM epochs were seen in our data).

The ROI(s) used for CSF analysis can include a ventricle of the brain, or other anatomical regions that contain CSF or are influenced by CSF flow. For instance, the ROI(s) could additionally or alternatively contain perivascular spaces that are used for brain clearance. As one example for identifying a ventricle ROI, an ROI for the fourth ventricle and/or aqueduct can be defined anatomically based on the functional images contained in the magnetic resonance imaging data. An initial registration matrix between the functional and anatomical images can be calculated (e.g., using boundary-based registration). The registered anatomical image(s) can then be overlaid onto the functional image(s) to identify the approximate position of the ventricle/aqueduct. The brightest voxels on the functional image(s) can then be selected to identify the ventricle.

In some embodiments of the analysis of inflow dynamics, the ventricle ROI can be split into separate sub-ROIs within individual slices. For instance, the sub-ROIs can be generated based on the projection of the ventricle ROI onto the bottom four slices of the functional acquisition volume. The mean signal from the sub-ROI of the ventricle on each slice can then be extracted. To capture the range of signal fluctuations between low-flow and high-flow conditions, the signal magnitude can be calculated as the relative ratio of the 95th percentile and 5th percentile of the signal in each ROI over time.

In some implementations, the signals in the ROI can then be low-pass filtered to extract the low-frequency signals, generating output as low-frequency CSF signal data. The signals can be low-pass filtered to retain signals below a cutoff frequency selected from the range of 0.1 Hz to 5 Hz. For instance, the signals can be low-pass filtered below 0.1 Hz. As another example, the signals can be low-pass filtered below 1 Hz, or any other suitable frequency selected from the range of 0.1 Hz to 5 Hz. The CSF signals, which in some instances may be low-frequency CSF signals, can then be output by displaying and/or storing the CSF signals in a memory or other suitable data storage device or medium.

As another data source that can be used when generating the imaging-based biomarkers described in the present disclosure, BOLD signal derivatives can be computed from the BOLD signals, as indicated at step 614. As an example, the temporal derivative of the BOLD signals can be computed, generating output as BOLD signal derivative data. These data can also be thresholded to generate thresholded BOLD signal derivative data. As one example, the thresholding can be performed by multiplying the BOLD signal derivative data by "−1" and setting all of the negative values to zero. In this way, the thresholded BOLD signal derivative data will be representative of inflow, but not outflow, signals.

Using the extracted signals, one or more imaging-based biomarkers are then generated, as indicated at step 616. For instance, the imaging-based biomarker can be generated based on a combination of two or more of the BOLD signals, the CSF signals, the slow-wave EEG signals, the BOLD signal derivates, or other signals or parameters extracted or computed from the extracted signals, the magnetic resonance imaging data, and/or the EEG data. As one example, the imaging-based biomarker can be generated based on the BOLD signals and the CSF signals. As another example, the imaging-based biomarker can be generated based on the BOLD signals, the CSF signals, and the slow-wave EEG signals. As yet another example, the imaging-based biomarker can be generated based on the BOLD signals, the CSF signals, the slow-wave EEG data, and the BOLD signal derivatives. In still other instances, the imaging-based biomarker may be based on a single extracted signal source, such as the CSF signals or the BOLD signals.

As an example, the imaging-based biomarker(s) can be generated by computing a comparison between two or more pairs of the extracted signal sources. The comparison can in some instances include, or otherwise be based on, a similarity measure or other measure of the coupling between the pairs of extracted signals sources. For example, the comparison can be based on a similarity measure such as a correlation, which may be a cross-correlation. In some instances, the extracted signal data can be spline detrended and normalized before computing the cross-correlations.

In one example, the power in the BOLD signals, CSF signals and/or the slow-wave EEG signals can be computed. For instance, a multi-taper spectral estimation can be used. The BOLD and CSF analyses can use a smaller number of tapers (e.g., 5 tapers) than the EEG analysis, which may use a larger number of tapers (e.g., 59 tapers). Power in the BOLD signals can be estimated in different segments, and the mean power in each subject can be across each segment. In some instances, pairwise comparisons for sleep and wake segments can be computed within subjects who exhibited both sleep and wake data, such as by using the Wilcoxon signed-rank test.

EEG analyses can use the occipital EEG channel identified as having good data quality in order to minimize ballistocardiogram artifact induced by motion in the magnetic field and to allow analysis of occipital alpha to track sleep onset.

When the imaging-based biomarker is based on a single extracted signal source, the method may include estimating or otherwise predicting another extracted signal source. For instance, the extracted signal source may be CSF signal data, from which BOLD signal data can be estimated or otherwise predicted. As another example, the extracted signal source may be BOLD signal data, from which CSF signal data can be estimated or otherwise predicted. In such instances, the underlying magnetic resonance imaging data may measure only one of CSF signals or BOLD signals, but using the methods described in the present disclosure the non-measured signals can be estimated or otherwise predicted.

The imaging-based biomarker(s) can then be output to a user, such as by displaying the imaging-based biomarker(s) or storing the imaging-based biomarker(s) for later use, as indicated at step 618. Other associated data (e.g., magnetic resonance images, parameter maps, EEG data, reports generated on such data) can also be output to the user.

Figure 7:
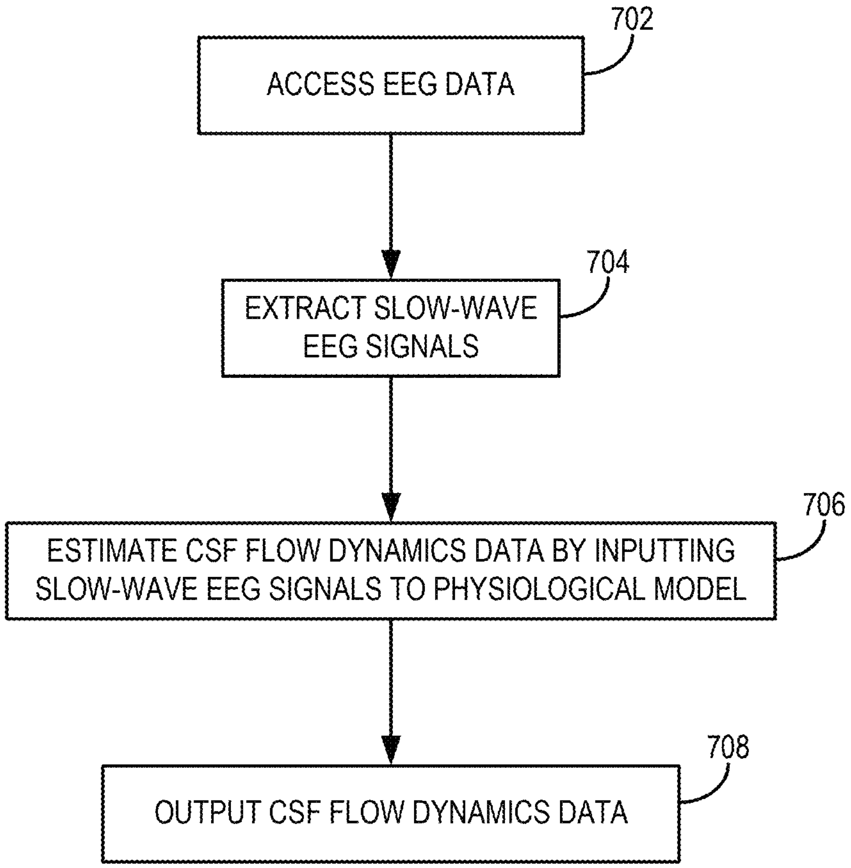
FIG. 7 is a flowchart setting forth the steps of an example method for estimating CSF flow dynamics from EEG data, according to some embodiments described in the present disclosure.

Referring now to FIG. 7 a flowchart is illustrated as setting forth the steps of an example method for estimating CSF flow dynamics by inputting EEG data to a physiological model, generating output as the estimated CSF flow dynamics.

The method includes accessing EEG data with a computer system, as indicated at step 702. Accessing the EEG may include retrieving such data from a memory or other suitable data storage device or medium. Alternatively, accessing the EEG may include acquiring such data with an EEG system and transferring or otherwise communicating the data to the computer system, which may be a part of the EEG system. In some embodiments, the EEG data are acquired contemporaneously with the magnetic resonance imaging data.

Slow-wave EEG signals are then extracted from the EEG data, as indicated at step 704. In this step, the EEG data can be processed to remove artifacts and/or filtered before extracting signals associated with slow-wave EEG signals.

As described above, gradient artifacts can be removed through average artifact subtraction using a moving average of the EEG data acquired within a previous number of TR periods during which the corresponding magnetic resonance imaging data were acquired. For instance, the number of TRs may be the previous 20 TRs. Electrodes can be re-referenced to this common average, computing this separately for electrodes contacting the head, and those placed on a reference layer. In some instances, channels on the cheeks and borders of a reference cap can be excluded from the common average.

As another example, ballistocardiogram artifacts can be removed using a regression of reference signals from isolated EEG electrodes. When there are a large number of noise electrodes as compared to signal electrodes, the regression can be performed after subsampling the noise electrodes (e.g., using only every fourth isolated electrode). Because the position and physiological noise influences on the electrodes can vary over long recording times, a dynamic time-varying regression of the reference signals can be implemented.

As another example, the EEG data can be filtered, such as by using a bandpass filter to remove unwanted frequency content while retaining the desired frequency content. For instance, the EEG data could be filtered using a bandpass filter having a passband of 0.2-4 Hz. As another example, the EEG data could be filtered into the 0.2-4 Hz band using a finite impulse response filter. In other implementations, a frequency band other than 0.2-4 Hz could also be used, such as 0.2-1 Hz or otherwise.

In some instances, the slow-wave EEG signal amplitudes can be extracted as the magnitude of the Hilbert transform, which can be smoothed, such as by using a moving average of 4 seconds. When extracting the slow-wave EEG signals, beta values for a best fit regression within sliding time windows can be fit using least-squares or another suitable regression technique. The sliding time windows can have a duration of 30 seconds, as one example, but other sliding window durations can also be used. The beta values can then be linearly interpolated over the non-overlapping windows. The resulting interpolated beta at every time point can then be used for a local subtraction of the reference signals from the modeled EEG recording. This regression can be performed individually for each EEG channel.

The slow-wave EEG signals, which may be slow-delta EEG envelope data, can then be output by displaying and/or storing the slow-wave EEG signals in a memory or other suitable data storage device or medium.

Figure 8:
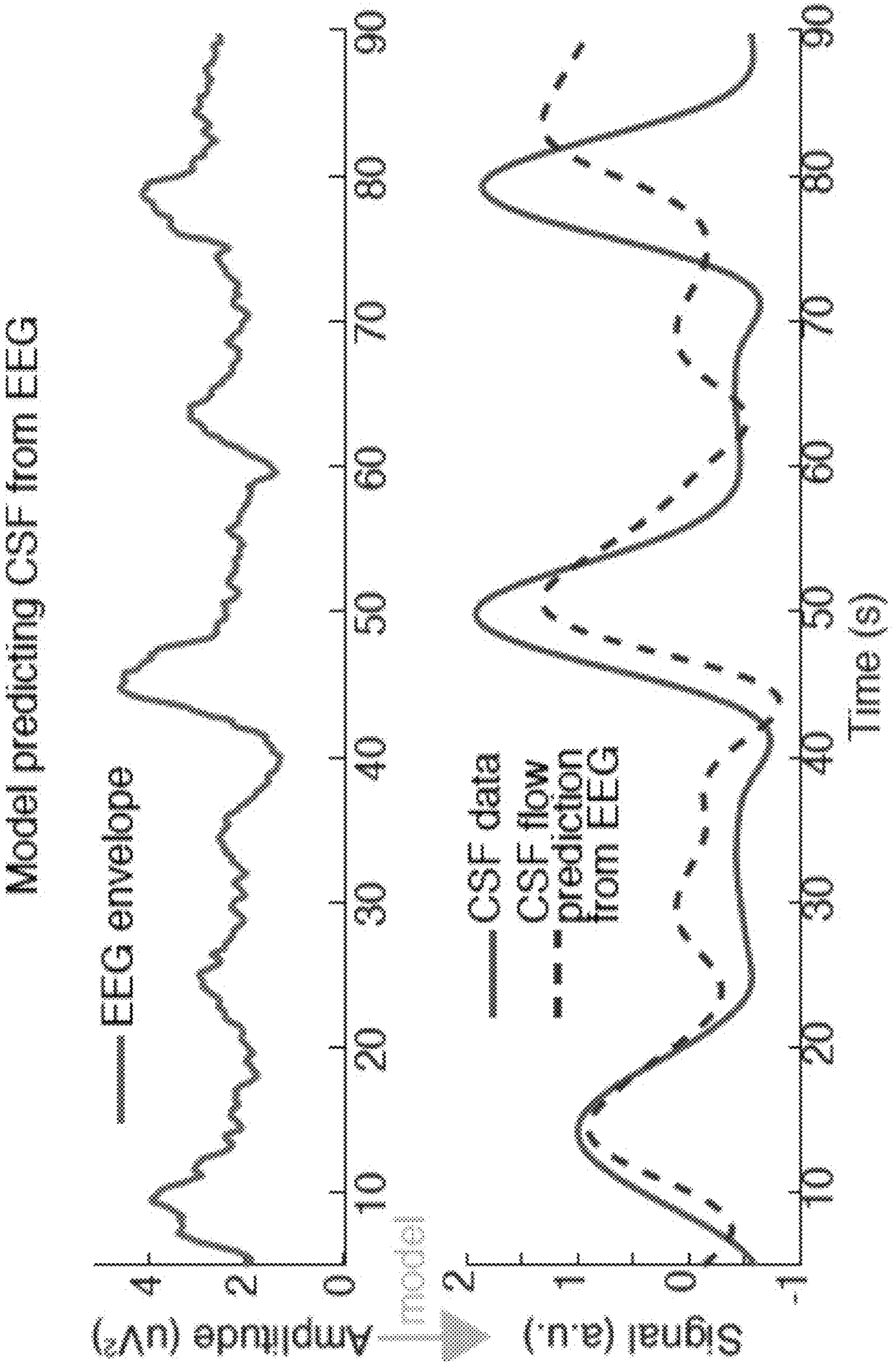
FIG. 8 shows an example time-series of the CSF signal prediction using the EEG power envelope.

The extracted slow-wave EEG signals can then by input to a physiological model, generating output as an estimate of CSF flow dynamics, as indicated at step 706. As described above, the physiological model can be constructed to link neural activity to CSF flow. In one example, the slow-wave EEG signals can be used to predict cerebral blood flow ("CBF") and cerebral metabolic rate of oxygen ("$CMRO_2$"). CBF alters cerebral blood volume ("CBV"), and together these produce the BOLD signal. The CBV changes are in turn used to predict changes in CSF volume and the measured CSF ("$CSF_m$") inflow signals. FIG. 8 shows an example time-series of the CSF signal prediction using the EEG power envelope.

The estimated CSF flow dynamics can then be output, as indicated at step 708. For instance, the CSF flow dynamics can be displayed to a user and/or stored for later use. As one example, the estimated CSF flow dynamics can be analyzed to assess a neurological and/or neurovascular state of a subject.

Figure 9:
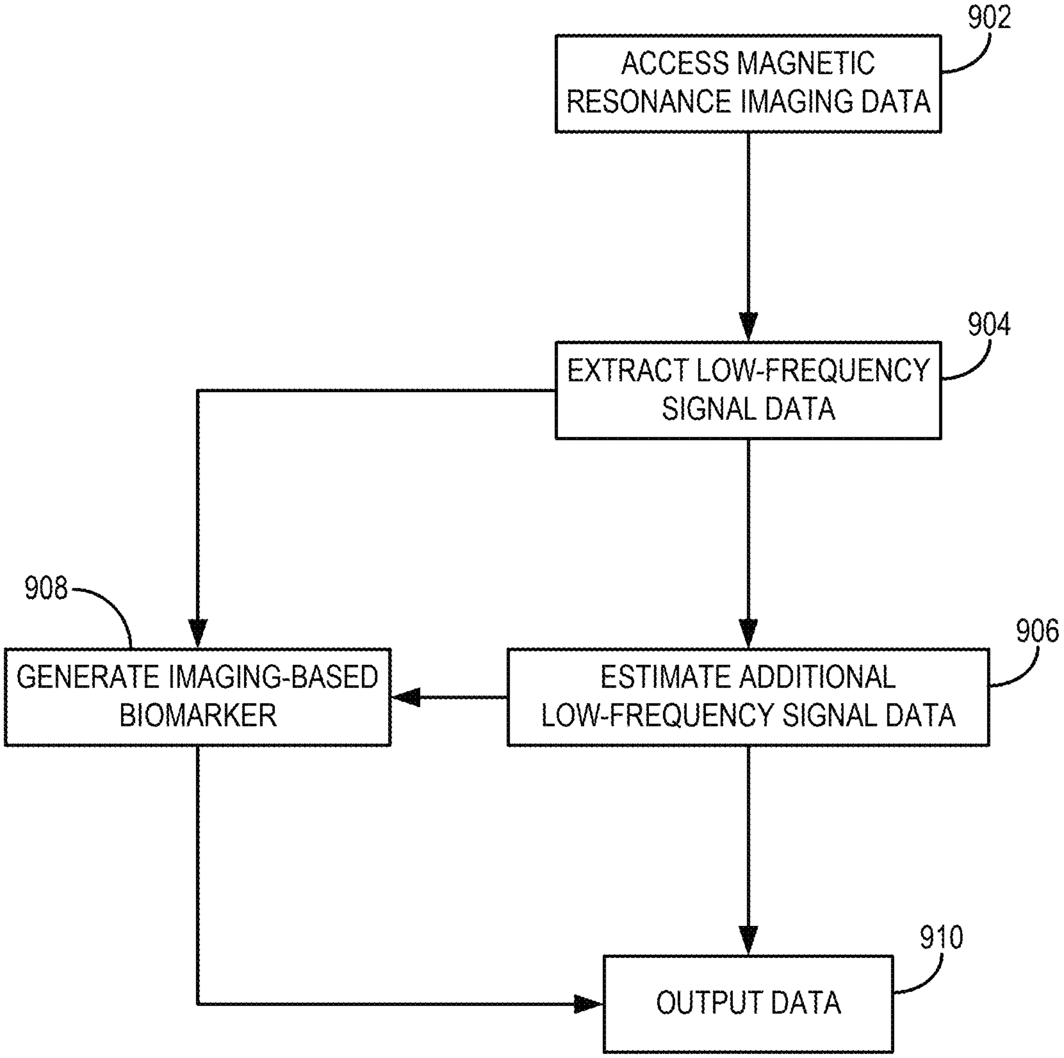
FIG. 9 is a flowchart setting forth the steps of an example method for estimating physiological signal data based on signals acquired from another coupled physiological source, and/or generating imaging-based biomarkers using one or both of those signal data.

Referring now to FIG. 9 a flowchart is illustrated as setting forth the steps of an example method for estimating CSF flow dynamics by inputting EEG data to a physiological model, generating output as the estimated CSF flow dynamics.

The method includes accessing magnetic resonance imaging data with a computer system, as indicated at step 902. Accessing the magnetic resonance imaging may include retrieving such data from a memory or other suitable data storage device or medium. Alternatively, accessing the magnetic resonance imaging may include acquiring such data with an MRI system and transferring or otherwise communicating the data to the computer system, which may be a part of the MRI system.

In general, the magnetic resonance imaging data can include data (e.g., k-space data) and/or images acquired with an MRI system. The magnetic resonance imaging data are acquired from a subject's brain. Further, the magnetic resonance imaging data can be acquired while the subject is in a sleep state or a wake state. In some instances, the magnetic resonance imaging data are acquired during both a sleep state and a wake state. By placing the edge of the acquisition volume at a region containing CSF, such as a ventricle (which in some non-limiting examples may be the fourth ventricle) or aqueduct, simultaneous measurement of CSF inflow signals and BOLD dynamics can be achieved.

As one example, the magnetic resonance imaging data can include both functional imaging data and anatomical imaging data. For instance, the magnetic resonance imaging data can be acquired using a multi-echo MPRAGE sequence, and in some instances can include acquiring data with isotropic resolution (e.g., 1 mm isotropic resolution). The anatomical data can assist with identifying the CSF spaces, such as ventricles, near which the functional data should be acquired.

Functional data can be acquired over an imaging volume (e.g., 40 slices) with isotropic resolution (e.g., 2.5 $mm^3$ isotropic voxels). Such an acquisition volume can cover most of the brain, or a smaller part of the brain. fMRI scanning can include a single-shot gradient echo SMS-EPI sequence with MultiBand factor=8, matrix=92×92, blipped CAIPI shift=4, TR=367 ms, nominal echo-spacing=0.53 ms, flip angle=32-37, no in-plane acceleration. To achieve high temporal resolution imaging, accelerated data acquisition techniques can be used to acquire data at fast rates (e.g., TR <800 ms).

Physiological signal data representative of a first physiological source are then extracted from the magnetic resonance imaging data, as indicated at step 904. As one example, the physiological signal data can be CSF signal data. As another example, the physiological signal data can be BOLD signal data. In either instance, the methods described above for extracting such signal data can be used. For example, one or more anatomical ROIs can be selected and signals extracted from those ROIs. In some implementations, the signals can also be filtered to generate the respective low-frequency signal data. As described above, a low-pass filter having a cutoff frequency in a range of 0.1 Hz to 5 Hz can be used.

The extracted physiological signal data can then used to estimate or otherwise predict additional physiological signal data representative of a second physiological source, as indicated at step 906. For instance, CSF signal data can be used to estimate or otherwise predict BOLD signal data. As another example, BOLD signal data can be used to estimate or otherwise predict CSF signal data. In these instances, the first and second physiological sources correspond to different physiological processes (e.g., CSF flow dynamics and hemodynamics). In other implementations, the first and second physiological sources may correspond to the same physiological process, but correspond to different physiological states. For example, the first physiological source may be CSF flow dynamics during a sleep state, and the second physiological source may be CSF flow dynamics during a wake state.

In some instances, a physiological model can be used to estimate the additional physiological signal data. For example, the physiological model may describe a coupling between CSF flow dynamics and hemodynamic changes in the brain. As described above, such a model can be constructed based on observed coupling between CSF flow dynamics and hemodynamics changes that occur during sleep. This coupling mechanism can be applied to data acquired during a sleep state, a wake state, or both, to estimate signals from one of the coupled physiological sources when data have been acquired from the other coupled physiological source. Such a model can be used to estimate BOLD signals by inputting CSF signals to the model, generating output as the additional physiological signal data. Additionally or alternatively, such a model can be used to estimate CSF signals by inputting BOLD signals to the model, generating output as the additional physiological signal data.

In some implementations, the extracted physiological signal data and/or the estimated additional physiological signal data can be used to generate an imaging-based biomarker, as indicated at step 908.

As one non-limiting example, the imaging-based biomarker can be generated based on one or both of the extracted physiological signal data or the estimated additional physiological signal data. For instance, the imaging-based biomarker may be generated by comparing the extracted physiological signal data to normative data, reference data, or the like. In such instances, the normative or reference data may be representative of a single or population-based example of a normal condition or state, or of an abnormal condition or state. For example, the normative and/or reference data may be representative of a particular neurological and/or neurovascular condition, such that comparison of the extracted physiological signal data to the normative and/or reference data can provide a calculated score value, or the like, that quantifies a similarity between the extracted physiological signal data and the normative and/or reference data. In such instances, this output can be the imaging-based biomarker.

As another example, the imaging-based biomarker(s) can be generated by computing a comparison between the extracted physiological signal data and the estimated additional physiological signal data. The comparison can in some instances include, or otherwise be based on, a similarity measure or other measure of the coupling between the pairs of extracted signals sources. For example, the comparison can be based on a similarity measure such as a correlation, which may be a cross-correlation. In some instances, the extracted signal data can be spline detrended and normalized before computing the cross-correlations.

As another example, the imaging-based biomarker can be generated by measuring temporal dynamics of the extracted signal. For example, the magnitude of the change in CSF flow in wakefulness versus sleep, or the timing and shape of CSF flow waves, could be used to predict neurological and/or neurovascular state.

The extracted physiological signal data, the estimated additional physiological signal data and/or the imaging-based biomarker can then be output, as indicated at step 910. For instance, the extracted physiological signal data, the estimated additional physiological signal data and/or the imaging-based biomarker can be displayed to a user and/or stored for later use.

Figure 10:
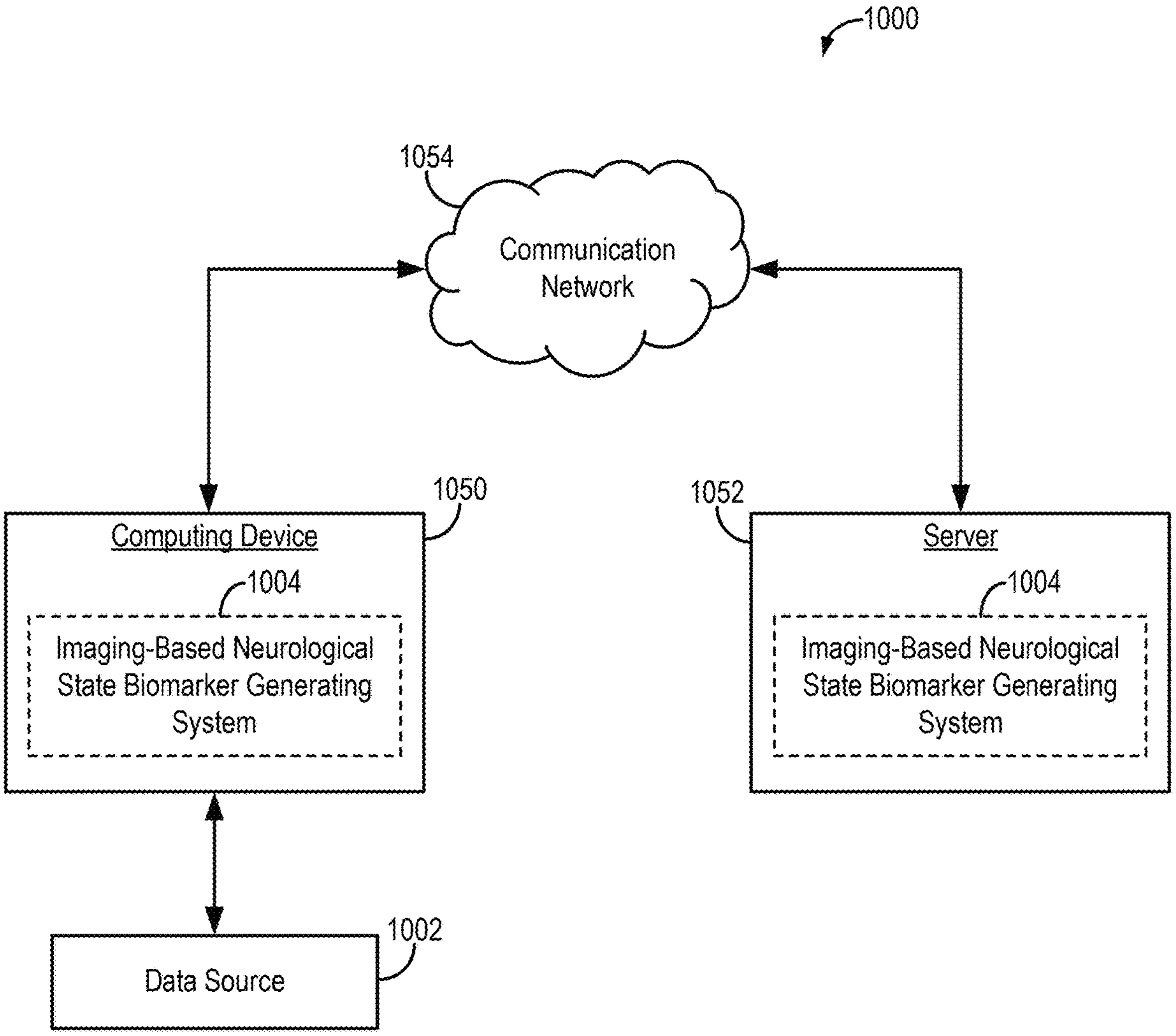
FIG. 10 is a block diagram of an example system for generating imaging-based biomarkers and/or estimating CSF flow dynamics according to embodiments described in the present disclosure.

Referring now to FIG. 10, an example of a system 1000 for generating imaging-based biomarkers indicative of a neurological state, which may include a neurovascular state or an assessment of drug delivery dynamics, of a subject in accordance with some embodiments of the systems and methods described in the present disclosure is shown. Additionally or alternatively, the system 1000 can be used to estimate or otherwise predict additional data from a single input signal source (e.g., estimating BOLD signal data from CSF signal data, estimating CSF signal data from slow-wave EEG signal data). As shown in FIG. 10, a computing device 1050 can receive one or more types of data (e.g., magnetic resonance imaging data, EEG data) from data source 1002, which may be a magnetic resonance imaging source, an EEG data source, and so on. In some embodiments, computing device 1050 can execute at least a portion of an imaging-based neurological state biomarker generating system 1004 to generate one or more imaging-based biomarkers, or to estimate additional signal data, from data received from the data source 1002.

Additionally or alternatively, in some embodiments, the computing device 1050 can communicate information about data received from the data source 1002 to a server 1052 over a communication network 1054, which can execute at least a portion of the imaging-based neurological state biomarker generating system 1004. In such embodiments, the server 1052 can return information to the computing device 1050 (and/or any other suitable computing device) indicative of an output of the imaging-based neurological state biomarker generating system 1004.

In some embodiments, computing device 1050 and/or server 1052 can be any suitable computing device or combination of devices, such as a desktop computer, a laptop computer, a smartphone, a tablet computer, a wearable computer, a server computer, a virtual machine being executed by a physical computing device, and so on. The computing device 1050 and/or server 1052 can also reconstruct images from the data.

In some embodiments, data source 1002 can be any suitable source of image data (e.g., measurement data, images reconstructed from measurement data), such as an MRI system, and EEG system, another computing device (e.g., a server storing image data), and so on. In some embodiments, data source 1002 can be local to computing device 1050. For example, data source 1002 can be incorporated with computing device 1050 (e.g., computing device 1050 can be configured as part of a device for capturing, scanning, and/or storing images). As another example, data source 1002 can be connected to computing device 1050 by a cable, a direct wireless link, and so on. Additionally or alternatively, in some embodiments, data source 1002 can be located locally and/or remotely from computing device 1050, and can communicate data to computing device 1050 (and/or server 1052) via a communication network (e.g., communication network 1054).

In some embodiments, communication network 1054 can be any suitable communication network or combination of communication networks. For example, communication network 1054 can include a Wi-Fi network (which can include one or more wireless routers, one or more switches, etc.), a peer-to-peer network (e.g., a Bluetooth network), a cellular network (e.g., a 3G network, a 4G network, etc., complying with any suitable standard, such as CDMA, GSM, LTE, LTE Advanced, WiMAX, etc.), a wired network, and so on. In some embodiments, communication network 1054 can be a local area network, a wide area network, a public network (e.g., the Internet), a private or semi-private network (e.g., a corporate or university intranet), any other suitable type of network, or any suitable combination of networks. Communications links shown in FIG. 10 can each be any suitable communications link or combination of communications links, such as wired links, fiber optic links, Wi-Fi links, Bluetooth links, cellular links, and so on.

Figure 11:
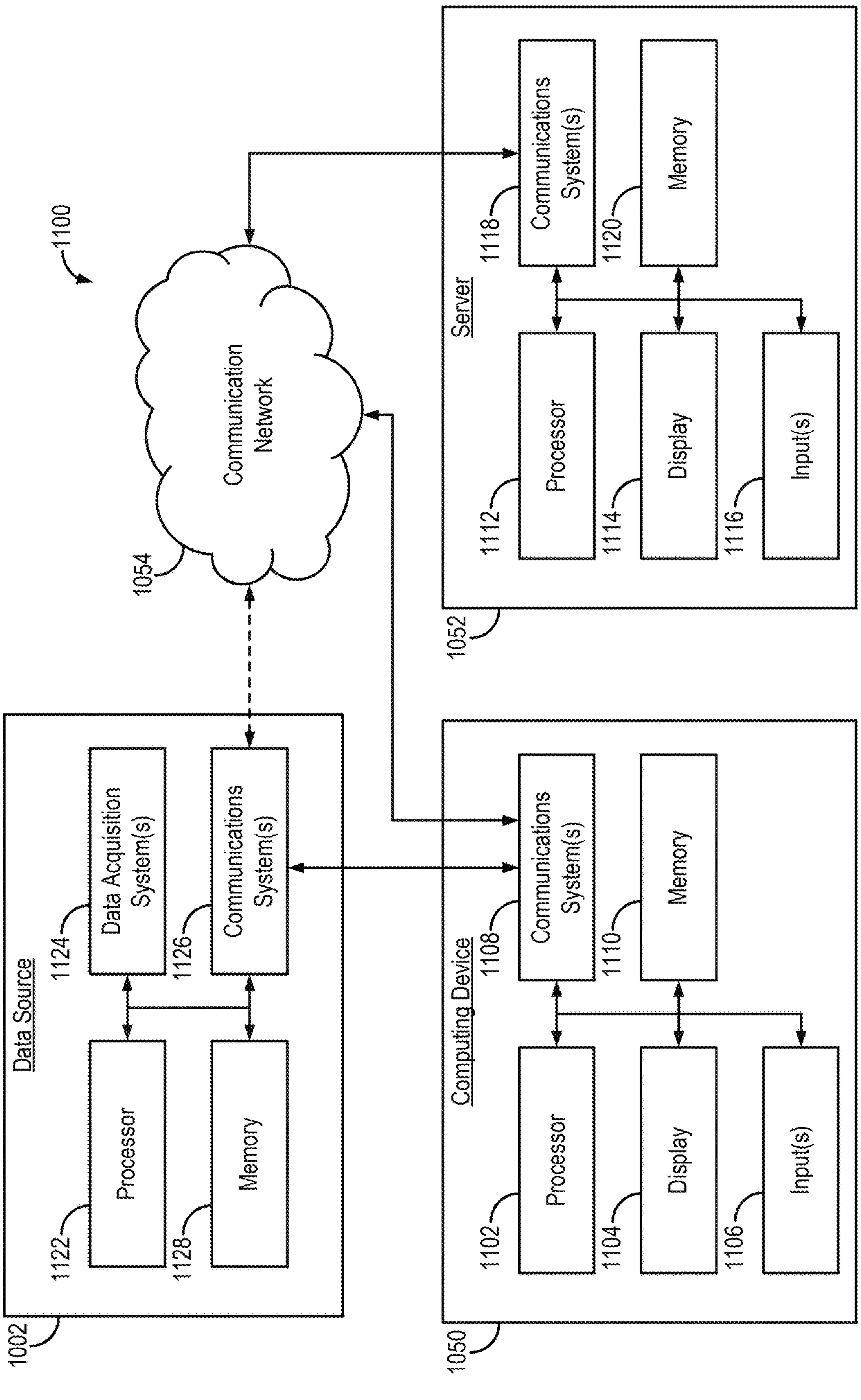
FIG. 11 is a block diagram of components that can implement the system of FIG. 10.

Referring now to FIG. 11, an example of hardware 1100 that can be used to implement data source 1002, computing device 1050, and server 1052 in accordance with some embodiments of the systems and methods described in the present disclosure is shown. As shown in FIG. 11, in some embodiments, computing device 1050 can include a processor 1102, a display 1104, one or more inputs 1106, one or more communication systems 1108, and/or memory 1110. In some embodiments, processor 1102 can be any suitable hardware processor or combination of processors, such as a central processing unit ("CPU"), a graphics processing unit ("GPU"), and so on. In some embodiments, display 1104 can include any suitable display devices, such as a computer monitor, a touchscreen, a television, and so on. In some embodiments, inputs 1106 can include any suitable input devices and/or sensors that can be used to receive user input, such as a keyboard, a mouse, a touchscreen, a microphone, and so on.

In some embodiments, communications systems 1108 can include any suitable hardware, firmware, and/or software for communicating information over communication network 1054 and/or any other suitable communication networks. For example, communications systems 1108 can include one or more transceivers, one or more communication chips and/or chip sets, and so on. In a more particular example, communications systems 1108 can include hardware, firmware and/or software that can be used to establish a Wi-Fi connection, a Bluetooth connection, a cellular connection, an Ethernet connection, and so on.

In some embodiments, memory 1110 can include any suitable storage device or devices that can be used to store instructions, values, data, or the like, that can be used, for example, by processor 1102 to present content using display 1104, to communicate with server 1052 via communications system(s) 1108, and so on. Memory 1110 can include any suitable volatile memory, non-volatile memory, storage, or any suitable combination thereof. For example, memory 1110 can include RAM, ROM, EEPROM, one or more flash drives, one or more hard disks, one or more solid state drives, one or more optical drives, and so on. In some embodiments, memory 1110 can have encoded thereon, or otherwise stored therein, a computer program for controlling operation of computing device 1050. In such embodiments, processor 1102 can execute at least a portion of the computer program to present content (e.g., images, user interfaces, graphics, tables), receive content from server 1052, transmit information to server 1052, and so on.

In some embodiments, server 1052 can include a processor 1112, a display 1114, one or more inputs 1116, one or more communications systems 1118, and/or memory 1120. In some embodiments, processor 1112 can be any suitable hardware processor or combination of processors, such as a CPU, a GPU, and so on. In some embodiments, display 1114 can include any suitable display devices, such as a computer monitor, a touchscreen, a television, and so on. In some embodiments, inputs 1116 can include any suitable input devices and/or sensors that can be used to receive user input, such as a keyboard, a mouse, a touchscreen, a microphone, and so on.

In some embodiments, communications systems 1118 can include any suitable hardware, firmware, and/or software for communicating information over communication network 1054 and/or any other suitable communication networks. For example, communications systems 1118 can include one or more transceivers, one or more communication chips and/or chip sets, and so on. In a more particular example, communications systems 1118 can include hardware, firmware and/or software that can be used to establish a Wi-Fi connection, a Bluetooth connection, a cellular connection, an Ethernet connection, and so on.

In some embodiments, memory 1120 can include any suitable storage device or devices that can be used to store instructions, values, data, or the like, that can be used, for example, by processor 1112 to present content using display 1114, to communicate with one or more computing devices 1050, and so on. Memory 1120 can include any suitable volatile memory, non-volatile memory, storage, or any suitable combination thereof. For example, memory 1120 can include RAM, ROM, EEPROM, one or more flash drives, one or more hard disks, one or more solid state drives, one or more optical drives, and so on. In some embodiments, memory 1120 can have encoded thereon a server program for controlling operation of server 1052. In such embodiments, processor 1112 can execute at least a portion of the server program to transmit information and/or content (e.g., data, images, a user interface) to one or more computing devices 1050, receive information and/or content from one or more computing devices 1050, receive instructions from one or more devices (e.g., a personal computer, a laptop computer, a tablet computer, a smartphone), and so on.

In some embodiments, data source 1002 can include a processor 1122, one or more data acquisition systems 1124, one or more communications systems 1126, and/or memory 1128. In some embodiments, processor 1122 can be any suitable hardware processor or combination of processors, such as a CPU, a GPU, and so on. In some embodiments, the one or more data acquisition systems 1124 are generally configured to acquire data, images, or both, and can include an MRI system, and EEG system, and so on. Additionally or alternatively, in some embodiments, one or more data acquisition systems 1124 can include any suitable hardware, firmware, and/or software for coupling to and/or controlling operations of an MRI system, an EEG system, and so on. In some embodiments, one or more portions of the one or more data acquisition systems 1124 can be removable and/or replaceable.

Note that, although not shown, data source 1002 can include any suitable inputs and/or outputs. For example, data source 1002 can include input devices and/or sensors that can be used to receive user input, such as a keyboard, a mouse, a touchscreen, a microphone, a trackpad, a trackball, and so on. As another example, data source 1002 can include any suitable display devices, such as a computer monitor, a touchscreen, a television, etc., one or more speakers, and so on.

In some embodiments, communications systems 1126 can include any suitable hardware, firmware, and/or software for communicating information to computing device 1050 (and, in some embodiments, over communication network 1054 and/or any other suitable communication networks). For example, communications systems 1126 can include one or more transceivers, one or more communication chips and/or chip sets, and so on. In a more particular example, communications systems 1126 can include hardware, firmware and/or software that can be used to establish a wired connection using any suitable port and/or communication standard (e.g., VGA, DVI video, USB, RS-232, etc.), Wi-Fi connection, a Bluetooth connection, a cellular connection, an Ethernet connection, and so on.

In some embodiments, memory 1128 can include any suitable storage device or devices that can be used to store instructions, values, data, or the like, that can be used, for example, by processor 1122 to control the one or more data acquisition systems 1124, and/or receive data from the one or more data acquisition systems 1124; to images from data; present content (e.g., images, a user interface) using a display; communicate with one or more computing devices 1050; and so on. Memory 1128 can include any suitable volatile memory, non-volatile memory, storage, or any suitable combination thereof. For example, memory 1128 can include RAM, ROM, EEPROM, one or more flash drives, one or more hard disks, one or more solid state drives, one or more optical drives, and so on. In some embodiments, memory 1128 can have encoded thereon, or otherwise stored therein, a program for controlling operation of data source 1002. In such embodiments, processor 1122 can execute at least a portion of the program to generate images, transmit information and/or content (e.g., data, images) to one or more computing devices 1050, receive information and/or content from one or more computing devices 1050, receive instructions from one or more devices (e.g., a personal computer, a laptop computer, a tablet computer, a smartphone, etc.), and so on.

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (e.g., hard disks, floppy disks), optical media (e.g., compact discs, digital video discs, Blu-ray discs), semiconductor media (e.g., random access memory ("RAM"), flash memory, electrically programmable read only memory ("EPROM"), electrically erasable programmable read only memory ("EEPROM")), any suitable media that is not fleeting or devoid of any semblance of permanence during transmission, and/or any suitable tangible media. As another example, transitory computer readable media can include signals on networks, in wires, conductors, optical fibers, circuits, or any suitable media that is fleeting and devoid of any semblance of permanence during transmission, and/or any suitable intangible media.

Figure 12:
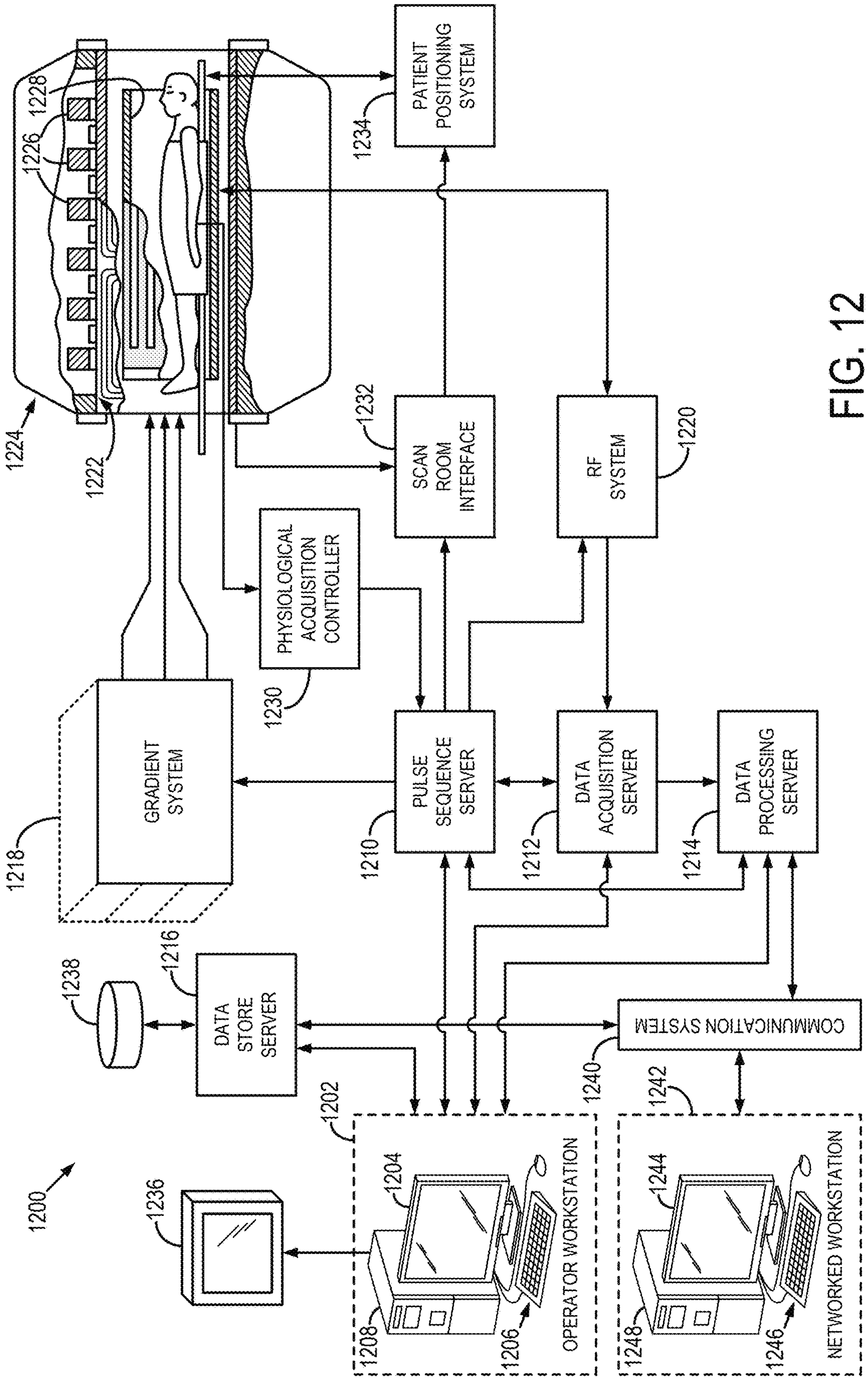
FIG. 12 is a block diagram of an example MRI system.

Referring particularly now to FIG. 12, an example of an MRI system 1200 that can implement the methods described here is illustrated. The MRI system 1200 includes an operator workstation 1202 that may include a display 1204, one or more input devices 1206 (e.g., a keyboard, a mouse), and a processor 1208. The processor 1208 may include a commercially available programmable machine running a commercially available operating system. The operator workstation 1202 provides an operator interface that facilitates entering scan parameters into the MRI system 1200. The operator workstation 1202 may be coupled to different servers, including, for example, a pulse sequence server 1210, a data acquisition server 1212, a data processing server 1214, and a data store server 1216. The operator workstation 1202 and the servers 1210, 1212, 1214, and 1216 may be connected via a communication system 1240, which may include wired or wireless network connections.

The pulse sequence server 1210 functions in response to instructions provided by the operator workstation 1202 to operate a gradient system 1218 and a radiofrequency ("RF") system 1220. Gradient waveforms for performing a prescribed scan are produced and applied to the gradient system 1218, which then excites gradient coils in an assembly 1222 to produce the magnetic field gradients $G_x$, $G_y$, and $G_z$ that are used for spatially encoding magnetic resonance signals. The gradient coil assembly 1222 forms part of a magnet assembly 1224 that includes a polarizing magnet 1226 and a whole-body RF coil 1228.

RF waveforms are applied by the RF system 1220 to the RF coil 1228, or a separate local coil to perform the prescribed magnetic resonance pulse sequence. Responsive magnetic resonance signals detected by the RF coil 1228, or a separate local coil, are received by the RF system 1220. The responsive magnetic resonance signals may be amplified, demodulated, filtered, and digitized under direction of commands produced by the pulse sequence server 1210. The RF system 1220 includes an RF transmitter for producing a wide variety of RF pulses used in MRI pulse sequences. The RF transmitter is responsive to the prescribed scan and direction from the pulse sequence server 1210 to produce RF pulses of the desired frequency, phase, and pulse amplitude waveform. The generated RF pulses may be applied to the whole-body RF coil 1228 or to one or more local coils or coil arrays.

The RF system 1220 also includes one or more RF receiver channels. An RF receiver channel includes an RF preamplifier that amplifies the magnetic resonance signal received by the coil 1228 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M = \sqrt{I^2 + Q^2}; \tag{6}$$

and the phase of the received magnetic resonance signal may also be determined according to the following relationship:

$$\varphi = \tan^{-1}\left(\frac{Q}{I}\right). \tag{7}$$

The pulse sequence server 1210 may receive patient data from a physiological acquisition controller 1230. By way of example, the physiological acquisition controller 1230 may receive signals from a number of different sensors connected to the patient, including electrocardiograph ("ECG") signals from electrodes, or respiratory signals from a respiratory bellows or other respiratory monitoring devices. These signals may be used by the pulse sequence server 1210 to synchronize, or "gate," the performance of the scan with the subject's heart beat or respiration.

The pulse sequence server 1210 may also connect to a scan room interface circuit 1232 that receives signals from various sensors associated with the condition of the patient and the magnet system. Through the scan room interface circuit 1232, a patient positioning system 1234 can receive commands to move the patient to desired positions during the scan.

The digitized magnetic resonance signal samples produced by the RF system 1220 are received by the data acquisition server 1212. The data acquisition server 1212 operates in response to instructions downloaded from the operator workstation 1202 to receive the real-time magnetic resonance data and provide buffer storage, so that data is not lost by data overrun. In some scans, the data acquisition server 1212 passes the acquired magnetic resonance data to the data processor server 1214. In scans that require information derived from acquired magnetic resonance data to control the further performance of the scan, the data acquisition server 1212 may be programmed to produce such information and convey it to the pulse sequence server 1210. For example, during pre-scans, magnetic resonance data may be acquired and used to calibrate the pulse sequence performed by the pulse sequence server 1210. As another example, navigator signals may be acquired and used to adjust the operating parameters of the RF system 1220 or the gradient system 1218, or to control the view order in which k-space is sampled. In still another example, the data acquisition server 1212 may also process magnetic resonance signals used to detect the arrival of a contrast agent in a magnetic resonance angiography ("MRA") scan. For example, the data acquisition server 1212 may acquire magnetic resonance data and processes it in real-time to produce information that is used to control the scan.

The data processing server 1214 receives magnetic resonance data from the data acquisition server 1212 and processes the magnetic resonance data in accordance with instructions provided by the operator workstation 1202. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 1214 are conveyed back to the operator workstation 1202 for storage. Real-time images may be stored in a data base memory cache, from which they may be output to operator display 1202 or a display 1236. Batch mode images or selected real time images may be stored in a host database on disc storage 1238. When such images have been reconstructed and transferred to storage, the data processing server 1214 may notify the data store server 1216 on the operator workstation 1202. The operator workstation 1202 may be used by an operator to archive the images, produce films, or send the images via a network to other facilities.

The MRI system 1200 may also include one or more networked workstations 1242. For example, a networked workstation 1242 may include a display 1244, one or more input devices 1246 (e.g., a keyboard, a mouse), and a processor 1248. The networked workstation 1242 may be located within the same facility as the operator workstation 1202, or in a different facility, such as a different healthcare institution or clinic.

The networked workstation 1242 may gain remote access to the data processing server 1214 or data store server 1216 via the communication system 1240. Accordingly, multiple networked workstations 1242 may have access to the data processing server 1214 and the data store server 1216. In this manner, magnetic resonance data, reconstructed images, or other data may be exchanged between the data processing server 1214 or the data store server 1216 and the networked workstations 1242, such that the data or images may be remotely processed by a networked workstation 1242.

The present disclosure has described one or more preferred embodiments, and it should be appreciated that many equivalents, alternatives, variations, and modifications, aside from those expressly stated, are possible and within the scope of the invention.

The invention claimed is:

1. A method for generating an imaging-based biomarker indicative of a temporal coupling between CSF waves and hemodynamic waves of a subject, the method comprising:

(a) acquiring magnetic resonance imaging data from the subject using a magnetic resonance imaging (MRI) system while the subject is in at least one of a sleep state or a wake state;

(b) generating blood-oxygenation-level dependent (BOLD) signal data by extracting a time series of BOLD signals from the magnetic resonance imaging data using a computer system comprising at least one processor and memory;

(c) generating cerebrospinal fluid (CSF) signal data by extracting a time series of CSF signals from the magnetic resonance imaging data using the computer system;

(d) generating the imaging-based biomarker by using the computer system to compute a cross-correlation between the BOLD signal data and the CSF signal data, wherein the imaging-based biomarker characterizes the temporal coupling between the CSF waves and the hemodynamic waves of the subject; and (e) displaying the imaging-based biomarker using the computer system, wherein the imaging-based biomarker is representative of at least one of a cognitive neurodegeneration, a sleep disturbance of the subject, or a neurological state that is representative of drug delivery dynamics.

2. The method of claim 1, wherein generating the BOLD signal data comprises identifying one or more gray matter regions-of-interest (ROIs) that contain gray matter in the subject's brain, and extracting the BOLD signals from the one or more gray matter ROIs.

3. The method of claim 2, wherein generating the BOLD signal data comprises applying a low-pass filter to the magnetic resonance imaging data in the one or more gray matter ROIs, generating output as low-frequency BOLD signal data.

4. The method of claim 1, wherein generating the CSF signal data comprises identifying one or more CSF-containing regions-of-interest (ROIs) in the subject's brain, and extracting the CSF signals from the one or more CSF-containing ROIs.

5. The method of claim 4, wherein the one or more CSF-containing ROIs include at least one of:

an ROI that contains a ventricle in the subject's brain;

an ROI that contains an aqueduct in the subject's brain; or an ROI that contains one or more perivascular spaces in the subject's brain.

6. The method of claim 4, wherein generating the CSF signal data comprises applying a low-pass filter to the magnetic resonance imaging data in the one or more CSF-containing ROIs, generating output as low-frequency CSF signal data.

7. The method of claim 1, further comprising:

acquiring electroencephalography (EEG) data from the subject's brain while the magnetic resonance imaging data are being acquired from the subject;

generating slow-delta wave EEG signal data from the EEG data by extracting slow-delta wave EEG signals having frequencies of 0.2-4 Hz from the EEG data using the computer system; and wherein generating the imaging-based biomarker comprises computing a comparison between at least two of the BOLD signal data, the CSF signal data, or the slow-delta wave EEG signal data.

8. The method of claim 7, further comprising:

identifying magnetic resonance imaging data acquired during at least one of a stable sleep period or a stable wake period; and wherein the BOLD signal data and the CSF signal data are generated from only the magnetic resonance imaging data acquired during the at least one of the stable sleep period or the stable wake period.

9. The method of claim 1, further comprising:

acquiring electroencephalography (EEG) data from the subject's brain while the magnetic resonance imaging data are being acquired from the subject;

generating slow-delta wave EEG signal data from the EEG data by extracting slow-delta wave EEG signals having frequencies of 0.2-4 Hz from the EEG data using the computer system; and generating BOLD signal derivative data by computing a derivative of the BOLD signal data using the computer system; and wherein generating the imaging-based biomarker comprises computing a comparison between at least two of the BOLD signal data, the CSF signal data, the slow-delta wave EEG signal data, or the BOLD signal derivative data.

10. The method of claim 9, wherein generating the imaging-based biomarker comprises computing a cross-correlation between the slow-delta wave EEG signal data and the BOLD signal derivative data.

11. The method of claim 9, wherein generating the BOLD signal derivative data comprises computing a temporal derivative of the magnetic resonance imaging data.

12. The method of claim 1, wherein the imaging-based biomarker characterizes the temporal coupling of CSF waves and hemodynamic waves to indicate the neurological state that is representative of drug delivery dynamics in the subject.

13. The method of claim 1, wherein the imaging-based biomarker characterizes the temporal coupling of CSF waves and hemodynamic waves to indicate a neurological state of the subject as a change in at least one of:

the CSF signal data; or a coupling between the CSF signal data and the BOLD signal data.

* * * * *